(12) United States Patent
Soucaille et al.

(10) Patent No.: US 8,911,978 B2
(45) Date of Patent: Dec. 16, 2014

(54) METHOD FOR THE PREPARATION OF HYDROXY ACIDS

(75) Inventors: Philippe Soucaille, Deyme (FR); Cedric Boisart, Gerzat (FR)

(73) Assignee: Metabolic Explorer, Saint Beauzire (FR)

( * ) Notice: Subject to any disclaimer, the term of this patent is extended or adjusted under 35 U.S.C. 154(b) by 0 days.

(21) Appl. No.: 13/807,907

(22) PCT Filed: Jun. 28, 2011

(86) PCT No.: PCT/EP2011/060836
§ 371 (c)(1),
(2), (4) Date: Dec. 31, 2012

(87) PCT Pub. No.: WO2012/001003
PCT Pub. Date: Jan. 5, 2012

(65) Prior Publication Data
US 2013/0109067 A1    May 2, 2013

Related U.S. Application Data

(60) Provisional application No. 61/361,125, filed on Jul. 2, 2010.

(30) Foreign Application Priority Data

Jul. 2, 2010  (EP) ..................... 10305723

(51) Int. Cl.
| | | |
|---|---|---|
| *C12P 7/42* | (2006.01) |
| *C12N 15/63* | (2006.01) |
| *C12P 7/52* | (2006.01) |
| *C12N 9/02* | (2006.01) |
| *C12N 9/88* | (2006.01) |

(52) U.S. Cl.
CPC ... *C12P 7/42* (2013.01); *C12P 7/52* (2013.01); *C12N 9/0008* (2013.01); *C12N 15/63* (2013.01); *C12N 9/88* (2013.01)
USPC .................. 435/146; 435/252.3; 435/252.31; 435/252.32; 435/252.33

(58) Field of Classification Search
None
See application file for complete search history.

(56) References Cited

U.S. PATENT DOCUMENTS

| | | | |
|---|---|---|---|
| 7,745,195 | B2 | 6/2010 | Chateau et al. |
| 8,088,620 | B2 | 1/2012 | Bestel-Corre et al. |
| 8,168,434 | B2 | 5/2012 | Soucaille et al. |
| 8,236,994 | B2 | 8/2012 | Soucaille |
| 8,252,579 | B2 | 8/2012 | Meynial-Salles et al. |
| 8,389,250 | B2 | 3/2013 | Figge et al. |
| 2005/0054060 | A1 | 3/2005 | Chateau et al. |
| 2006/0270013 | A1 | 11/2006 | Chateau et al. |
| 2007/0072279 | A1 | 3/2007 | Meynial-Salles et al. |
| 2007/0087403 | A1 | 4/2007 | Bestel-Corre et al. |
| 2008/0076167 | A1 | 3/2008 | Gokarn et al. |
| 2008/0085558 | A1 | 4/2008 | Soucaille et al. |
| 2008/0233617 | A1 | 9/2008 | Figge et al. |
| 2008/0286840 | A1 | 11/2008 | Figge et al. |
| 2008/0311632 | A1 | 12/2008 | Figge et al. |
| 2009/0029424 | A1 | 1/2009 | Bestel-Corre et al. |
| 2009/0075351 | A1* | 3/2009 | Burk et al. ............... 435/141 |
| 2009/0155867 | A1 | 6/2009 | Soucaille |
| 2009/0325245 | A1 | 12/2009 | Soucaille et al. |
| 2010/0021978 | A1 | 1/2010 | Burk et al. |
| 2010/0086982 | A1 | 4/2010 | Soucaille |
| 2010/0137655 | A1 | 6/2010 | Soucaille |
| 2010/0151536 | A1* | 6/2010 | Baynes et al. ............ 435/128 |
| 2012/0190116 | A1 | 7/2012 | Soucaille et al. |

FOREIGN PATENT DOCUMENTS

| | | | |
|---|---|---|---|
| EP | 0658628 | A1 | 6/1995 |
| EP | 0620853 | B1 | 3/1996 |
| EP | 0789023 | A2 | 8/1997 |
| EP | 0931833 | A2 | 7/1999 |
| EP | 1416063 | A1 | 5/2004 |
| JP | 2007082476 | A | 4/2007 |
| KR | 20110070763 | A | 6/2011 |
| WO | 9300440 | A1 | 1/1993 |
| WO | 9837050 | A1 | 8/1998 |
| WO | 0116346 | A1 | 3/2001 |
| WO | 0242418 | A2 | 5/2002 |
| WO | 03062173 | A2 | 7/2003 |
| WO | 03064366 | A1 | 8/2003 |
| WO | 2004076398 | A1 | 9/2004 |
| WO | 2004076659 | A2 | 9/2004 |
| WO | 2005047498 | A1 | 5/2005 |
| WO | 2005073364 | A2 | 8/2005 |
| WO | 2005111202 | A1 | 11/2005 |
| WO | 2005118719 | A2 | 12/2005 |
| WO | 2006022664 | A2 | 3/2006 |

(Continued)

OTHER PUBLICATIONS

Plaza et al. FEMS Microbiol. Lett. (2004) 238, 367-374.*
International Search Report for PCT/EP2011/060836 Mailed Jul. 29, 2011.
International Preliminary Report on Patentability for PCT/EP2011/060836 Completed Feb. 2, 2012.

(Continued)

*Primary Examiner* — Nashaat Nashed
(74) *Attorney, Agent, or Firm* — Miles and Stockbridge

(57) ABSTRACT

The present invention concerns a modified microorganism for the biological preparation of an hydroxy acid of formula (I) wherein the microorganism comprises a two-step metabolic pathway for the production of the said hydroxy acid from a hydroxy keto-acid of formula (II) through an intermediate hydroxy-aldehyde of formula (III), wherein EA1 is an enzyme having a 2-keto-acid decarboxylase activity, and EA2 is an enzyme having hydroxy aldehyde dehydrogenase activity.

The invention also concerns a method for the fermentative production of a hydroxy acid.

14 Claims, 3 Drawing Sheets

(56) References Cited

FOREIGN PATENT DOCUMENTS

| | | | |
|---|---|---|---|
| WO | 2006064611 A1 | 6/2006 |
| WO | 2006082252 A2 | 8/2006 |
| WO | 2006082254 A2 | 8/2006 |
| WO | 2007017710 A1 | 2/2007 |
| WO | 2007040548 A2 | 4/2007 |
| WO | 2007077041 A1 | 7/2007 |
| WO | 2007141316 A2 | 12/2007 |
| WO | 2007144346 A1 | 12/2007 |
| WO | 2008015885 A1 | 2/2008 |
| WO | 2008027742 A1 | 3/2008 |
| WO | 2008040387 A1 | 4/2008 |
| WO | 2008052595 A1 | 5/2008 |
| WO | 2008052973 A2 | 5/2008 |
| WO | 2008091627 A2 | 7/2008 |
| WO | 2008115840 A2 | 9/2008 |
| WO | 2009061477 A1 | 5/2009 |

OTHER PUBLICATIONS

Datsenko et al., "One-Step Inactivation of Chromosomal Genes in *Escherichia coli* K-12 Using PCR Products," Proc. Acad. Sci., USA, vol. 97, No. 12, pp. 6640-6645, (Jun. 6, 2000).

Anderson, "Growth Requirements of Virus-Resistant Mutants of *Escherichia coli* Strain "B"," Proc. Natl. Acad. Sci. USA, vol. 32, pp. 120-128, (Mar. 21, 1946).

Schaefer et al., "Automated Sampling Device for Monitoring Intracellular Metabolite Dynamics, " Analytical Biochemistry, vol. 279, pp. 88-96, (1999).

Liebl et al.; "Requirement of Chelating Compounds for the Growth of *Corynebacterium glutamicum* in Synthetic Media," Appl. Microbiol. Biotechnol, vol. 32, pp. 205-210, (1989).

Riedel et al., "Characterization of the Phosphoenolpyruvate Carboxykinase Gene From *Corynebacterium glutamicum* and Significance of the Enzyme for Growth and Amino Acid Production," J. Mol. Microbiol. Biotechnol. vol. 3, No. 4, pp. 573-583, (2001).

Ballou et al.,"The Synthesis and Properties of Hydroxypyruvic Acid Phosphate," J. Am. Chem. Soc. vol. 78, No. 15, pp. 3718-3720, (Feb. 27, 1956).

Kovach et al., "Four New Derivatives of the Broad-Host-Range Cloning Vector pBBR1MCS, Carying Different Antibiotic-Resistance Cassettes," Gene, vol. 166, pp. 175-176, (1995).

Harrington et al.; "Balanced Branching in Transcription Termination," Proc. Natl. Acad. Sci. USA, vol. 98, No. 9, pp. 5019-5024, (Apr. 24, 2001).

European Search Report for EP 10 30 5723 Date of Completion May 24, 2011.

Keon et al., "Recombinant Vector for Use in Transforming Recombinant Mocroorganism for Producing 3-Hydroxypropionic Acid, Comprises Glycerol-Dehdratase Coding Gene, Glycerol-Dehydratase Reactivation Factor-AB Gene or Aldehyde Dehydroginase Gene," Database WPI, Week 201013, Thomson Scientific, XP002638563, (2010).

* cited by examiner

SEQUENCE LISTING

```
<160> NUMBER OF SEQ ID NOS: 54

<210> SEQ ID NO 1
<211> LENGTH: 39
<212> TYPE: DNA
<213> ORGANISM: Artificial Sequence
<220> FEATURE:
<223> OTHER INFORMATION: Oligonucleotide

<400> SEQUENCE: 1
cccaagcttt gacttctatg tataccgtgg gtgattatc                             39

<210> SEQ ID NO 2
<211> LENGTH: 34
<212> TYPE: DNA
<213> ORGANISM: Artificial Sequence
<220> FEATURE:
<223> OTHER INFORMATION: Oligonucleotide

<400> SEQUENCE: 2
ggaattctta gcttttattc tgttcggcga acag                                 34

<210> SEQ ID NO 3
<211> LENGTH: 38
<212> TYPE: DNA
<213> ORGANISM: Artificial Sequence
<220> FEATURE:
<223> OTHER INFORMATION: Oligonucleotide

<400> SEQUENCE: 3
cccaagcttt gacttctatg aaacttaacg acagtaac                             38

<210> SEQ ID NO 4
<211> LENGTH: 44
<212> TYPE: DNA
<213> ORGANISM: Artificial Sequence
<220> FEATURE:
<223> OTHER INFORMATION: Oligonucleotide
```

-continued

<400> SEQUENCE: 4
gtgggtttaa acggaattct taaagaccga tgcacatata tttg          44

<210> SEQ ID NO 5
<211> LENGTH: 40
<212> TYPE: DNA
<213> ORGANISM: Artificial Sequence
<220> FEATURE:
<223> OTHER INFORMATION: Oligonucleotide

<400> SEQUENCE: 5
cccaagcttt gatggctcaa atcttcaatt ttagttctgg          40

<210> SEQ ID NO 6
<211> LENGTH: 35
<212> TYPE: DNA
<213> ORGANISM: Artificial Sequence
<220> FEATURE:
<223> OTHER INFORMATION: Oligonucleotide

<400> SEQUENCE: 6
ggaattctta accgtgacgg cgttcgaact caacc          35

<210> SEQ ID NO 7
<211> LENGTH: 37
<212> TYPE: DNA
<213> ORGANISM: Artificial Sequence
<220> FEATURE:
<223> OTHER INFORMATION: Oligonucleotide

<400> SEQUENCE: 7
cccaagcttt gatgggattg actactaaac ctctatc          37

<210> SEQ ID NO 8
<211> LENGTH: 34
<212> TYPE: DNA
<213> ORGANISM: Artificial Sequence
<220> FEATURE:
<223> OTHER INFORMATION: Oligonucleotide

<400> SEQUENCE: 8
gggatcctta ccatttcaac agatcgtcct tagc          34

<210> SEQ ID NO 9
<211> LENGTH: 104
<212> TYPE: DNA
<213> ORGANISM: Artificial Sequence
<220> FEATURE:
<223> OTHER INFORMATION: Oligonucleotide

<400> SEQUENCE: 9
agaactagtg agctgttgac aattaatcat ccggctcgta taatgtgtgg aagtcgacgg          60
atcctaagga ggttatataat gaacaacttt aatctgcaca cccc          104

<210> SEQ ID NO 10
<211> LENGTH: 86
<212> TYPE: DNA
<213> ORGANISM: Artificial Sequence
<220> FEATURE:
<223> OTHER INFORMATION: Oligonucleotide

<400> SEQUENCE: 10
gagcccgggg cagaaaggcc caccgaagg tgagccagtg tgatacgtag aattcttaat          60
taagttagct tttattctgt tcggcg          86

```
<210> SEQ ID NO 11
<211> LENGTH: 61
<212> TYPE: DNA
<213> ORGANISM: Artificial Sequence
<220> FEATURE:
<223> OTHER INFORMATION: Oligonucleotide

<400> SEQUENCE: 11
acgcgtcgac ggatcctaag gaggttataa atgaatttc atcatctggc ttactggcag    60
g                                                                    61

<210> SEQ ID NO 12
<211> LENGTH: 55
<212> TYPE: DNA
<213> ORGANISM: Artificial Sequence
<220> FEATURE:
<223> OTHER INFORMATION: Oligonucleotide

<400> SEQUENCE: 12
ctagctagcg aattcttaat taagtcaggc ctccaggctt atccagatgg ttttc          55

<210> SEQ ID NO 13
<211> LENGTH: 61
<212> TYPE: DNA
<213> ORGANISM: Artificial Sequence
<220> FEATURE:
<223> OTHER INFORMATION: Oligonucleotide

<400> SEQUENCE: 13
acgcgtcgac ggatcctaag gaggttataa atgaaactta acgacagtaa cttattccgc    60
c                                                                    61

<210> SEQ ID NO 14
<211> LENGTH: 54
<212> TYPE: DNA
<213> ORGANISM: Artificial Sequence
<220> FEATURE:
<223> OTHER INFORMATION: Oligonucleotide

<400> SEQUENCE: 14
ctagctagcg aattcttaat taagttaaag accgatgcac atatatttga tttc           54

<210> SEQ ID NO 15
<211> LENGTH: 54
<212> TYPE: DNA
<213> ORGANISM: Artificial Sequence
<220> FEATURE:
<223> OTHER INFORMATION: Oligonucleotide

<400> SEQUENCE: 15
acgcgtcgac ggatcctaag gaggttataa atgttcagta gatctacgct ctgc           54

<210> SEQ ID NO 16
<211> LENGTH: 51
<212> TYPE: DNA
<213> ORGANISM: Artificial Sequence
<220> FEATURE:
<223> OTHER INFORMATION: Oligonucleotide

<400> SEQUENCE: 16
ctagctagcg aattcttaat taagttactc gtccaatttg gcacggaccg c              51

<210> SEQ ID NO 17
<211> LENGTH: 98
<212> TYPE: DNA
```

```
<213> ORGANISM: Artificial Sequence
<220> FEATURE:
<223> OTHER INFORMATION: Oligonucleotide

<400> SEQUENCE: 17
cccatccttc tcaacttaaa gactaagact gtcatgaaaa agaccaaaat tgtttgcacc    60
atcggaccga aaaccgaatg taggctggag ctgcttcg                           98

<210> SEQ ID NO 18
<211> LENGTH: 99
<212> TYPE: DNA
<213> ORGANISM: Artificial Sequence
<220> FEATURE:
<223> OTHER INFORMATION: Oligonucleotide

<400> SEQUENCE: 18
ggacgtgaac agatgcggtg ttagtagtgc cgctcggtac cagtgcacca gaaaccataa   60
ctacaacgtc acctttgtgc atatgaatat cctcccttag                         99

<210> SEQ ID NO 19
<211> LENGTH: 22
<212> TYPE: DNA
<213> ORGANISM: Artificial Sequence
<220> FEATURE:
<223> OTHER INFORMATION: Oligonucleotide

<400> SEQUENCE: 19
gcgtaacctt ttccctggaa cg                                            22

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide

<400> SEQUENCE: 20
gcgttgctgg agcaacctgc cagc                                          24

<210> SEQ ID NO 21
<211> LENGTH: 31
<212> TYPE: DNA
<213> ORGANISM: Artificial Sequence
<220> FEATURE:
<223> OTHER INFORMATION: Oligonucleotide

<400> SEQUENCE: 21
ctagtctaga ttagtacagc agacgggcgc g                                  31

<210> SEQ ID NO 22
<211> LENGTH: 35
<212> TYPE: DNA
<213> ORGANISM: Artificial Sequence
<220> FEATURE:
<223> OTHER INFORMATION: Oligonucleotide

<400> SEQUENCE: 22
tcccccggga agcttccgtc agggcgtggt gaccg                              35

<210> SEQ ID NO 23
<211> LENGTH: 46
<212> TYPE: DNA
<213> ORGANISM: Artificial Sequence
<220> FEATURE:
<223> OTHER INFORMATION: Oligonucleotide
```

<400> SEQUENCE: 23
agcttacgta taaggaggta tattatggaa taccgtagcc tgacgc      46

<210> SEQ ID NO 24
<211> LENGTH: 113
<212> TYPE: DNA
<213> ORGANISM: Artificial Sequence
<220> FEATURE:
<223> OTHER INFORMATION: Oligonucleotide

<400> SEQUENCE: 24
gccccgggta gcagaaaggc ccacccgaag gtgagccagg agtatacatg aagcatttcc      60
gttaattaac ggagctcatc ctaggtcagg gtttcacacc aatttgcagc gcc      113

<210> SEQ ID NO 25
<211> LENGTH: 100
<212> TYPE: DNA
<213> ORGANISM: Artificial Sequence
<220> FEATURE:
<223> OTHER INFORMATION: Oligonucleotide

<400> SEQUENCE: 25
ttcgtgtgcc ggacgagcta cccgccgtca atttcttgcg tgaagaaaac gtctttgtga      60
tgacaacttc tcgtgcgtct tgtaggctgg agctgcttcg      100

<210> SEQ ID NO 26
<211> LENGTH: 100
<212> TYPE: DNA
<213> ORGANISM: Artificial Sequence
<220> FEATURE:
<223> OTHER INFORMATION: Oligonucleotide

<400> SEQUENCE: 26
atccagcgtt ggattcatgt gccgtagatc gtatggcgtg atctggtaga cgtaatagtt      60
gagccagttg gtaaacagta catatgaata tcctccttag      100

<210> SEQ ID NO 27
<211> LENGTH: 30
<212> TYPE: DNA
<213> ORGANISM: Artificial Sequence
<220> FEATURE:
<223> OTHER INFORMATION: Oligonucleotide

<400> SEQUENCE: 27
tcaccttcaa catgcaggct cgacattggc      30

<210> SEQ ID NO 28
<211> LENGTH: 30
<212> TYPE: DNA
<213> ORGANISM: Artificial Sequence
<220> FEATURE:
<223> OTHER INFORMATION: Oligonucleotide

<400> SEQUENCE: 28
ataaaaaagg cacccgaagg tgcctgaggt      30

<210> SEQ ID NO 29
<211> LENGTH: 122
<212> TYPE: DNA
<213> ORGANISM: Artificial Sequence
<220> FEATURE:
<223> OTHER INFORMATION: Oligonucleotide

<400> SEQUENCE: 29
cgggcaatat gtctctgtgt ggattaaaaa aagagtgtct gatagcagct tctgaactgg    60
ttaccttcct ggctcacctt cgggtgggcc tttctggtat actgtaggct ggagctgctt   120
cg                                                                  122

<210> SEQ ID NO 30
<211> LENGTH: 130
<212> TYPE: DNA
<213> ORGANISM: Artificial Sequence
<220> FEATURE:
<223> OTHER INFORMATION: Oligonucleotide

<400> SEQUENCE: 30
ccctgtcatt tttctccata atttcttcat aaaaaagccg ggctgcataa aagcaaaccc    60
ggcctgattg agataatgaa tagattcccg ggggaggcgc cgcggatcc catatgaata   120 tcctccttag                                                          130

<210> SEQ ID NO 31
<211> LENGTH: 27
<212> TYPE: DNA
<213> ORGANISM: Artificial Sequence
<220> FEATURE:
<223> OTHER INFORMATION: Oligonucleotide

<400> SEQUENCE: 31
gccatgccgc gctggtgttt ggtcgcg                                        27

<210> SEQ ID NO 32
<211> LENGTH: 24
<212> TYPE: DNA
<213> ORGANISM: Artificial Sequence
<220> FEATURE:
<223> OTHER INFORMATION: Oligonucleotide

<400> SEQUENCE: 32
gcgaccagaa ccagggaaag tgcg                                           24

<210> SEQ ID NO 33
<211> LENGTH: 35
<212> TYPE: DNA
<213> ORGANISM: Artificial Sequence
<220> FEATURE:
<223> OTHER INFORMATION: Oligonucleotide

<400> SEQUENCE: 33
tgctctagag tccgcgctgt gcaaatccag aatgg                               35

<210> SEQ ID NO 34
<211> LENGTH: 34
<212> TYPE: DNA
<213> ORGANISM: Artificial Sequence
<220> FEATURE:
<223> OTHER INFORMATION: Oligonucleotide

<400> SEQUENCE: 34
cccaagctta actctctaca acagaaataa aaac                                34

<210> SEQ ID NO 35
<211> LENGTH: 100
<212> TYPE: DNA
<213> ORGANISM: Artificial Sequence
<220> FEATURE:
<223> OTHER INFORMATION: Oligonucleotide

<400> SEQUENCE: 35
ctggctttca caaggccgta tggcgagcag gagaagcaaa ttcttactgc cgaagcggta    60
gaatttctga ctgagctggt tgtaggctgg agctgcttcg                          100

<210> SEQ ID NO 36
<211> LENGTH: 99
<212> TYPE: DNA
<213> ORGANISM: Artificial Sequence
<220> FEATURE:
<223> OTHER INFORMATION: Oligonucleotide

<400> SEQUENCE: 36
aacatcttcc acatgccctt cacgtatgcg gttttgtagt gcgcgccagt aatcagcgcg    60
gaacaggtcg gcgtgcatcc atatgaatat cctccttag                           99

<210> SEQ ID NO 37
<211> LENGTH: 24
<212> TYPE: DNA
<213> ORGANISM: Artificial Sequence
<220> FEATURE:
<223> OTHER INFORMATION: Oligonucleotide

<400> SEQUENCE: 37
cgttaagcga ttcagcacct tacc                                           24

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide

<400> SEQUENCE: 38
aacgcattac ccactctgtt taatacg                                        27

<210> SEQ ID NO 39
<211> LENGTH: 100
<212> TYPE: DNA
<213> ORGANISM: Artificial Sequence
<220> FEATURE:
<223> OTHER INFORMATION: Oligonucleotide

<400> SEQUENCE: 39
gcgctttgaa agcctggttg gactcttctt acctctctgg cgcaaaccag agctggatag    60
aacagctcta tgaagacttc tgtaggctgg agctgcttcg                          100

<210> SEQ ID NO 40
<211> LENGTH: 99
<212> TYPE: DNA
<213> ORGANISM: Artificial Sequence
<220> FEATURE:
<223> OTHER INFORMATION: Oligonucleotide

<400> SEQUENCE: 40
ccagcagcag acgcgtcgga tcttccagca actctttgat cgttaccagg aagcccacgg    60
attcgcgacc atcgatcagc atatgaatat cctccttag                           99

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide

```
<400> SEQUENCE: 41
ggcgtaacaa agaaatgcag g                                              21

<210> SEQ ID NO 42
<211> LENGTH: 18
<212> TYPE: DNA
<213> ORGANISM: Artificial Sequence
<220> FEATURE:
<223> OTHER INFORMATION: Oligonucleotide

<400> SEQUENCE: 42
gcttcaacca gaatctgg                                                  18

<210> SEQ ID NO 43
<211> LENGTH: 97
<212> TYPE: DNA
<213> ORGANISM: Artificial Sequence
<220> FEATURE:
<223> OTHER INFORMATION: Oligonucleotide

<400> SEQUENCE: 43
cccgcacatt cttatcgttg aagacgagtt ggtaacacgc aacacgttga aaagtatttt    60
cgaagcggaa ggctatgtgt aggctggagc tgcttcg                             97

<210> SEQ ID NO 44
<211> LENGTH: 99
<212> TYPE: DNA
<213> ORGANISM: Artificial Sequence
<220> FEATURE:
<223> OTHER INFORMATION: Oligonucleotide

<400> SEQUENCE: 44
ccagatcacc gcagaagcga taaccttcac cgtgaatggt ggcgatgatt tccggcgtat    60
ccggcgtaga ttcgaaatgc atatgaatat cctccttag                           99

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide

<400> SEQUENCE: 45
cgacaattgg attcaccacg                                                20

<210> SEQ ID NO 46
<211> LENGTH: 21
<212> TYPE: DNA
<213> ORGANISM: Artificial Sequence
<220> FEATURE:
<223> OTHER INFORMATION: Oligonucleotide

<400> SEQUENCE: 46
gcggtattga aaggttggtg c                                              21

<210> SEQ ID NO 47
<211> LENGTH: 70
<212> TYPE: DNA
<213> ORGANISM: Artificial Sequence
<220> FEATURE:
<223> OTHER INFORMATION: Oligonucleotide
```

```
<400> SEQUENCE: 47
taaacaacat aagcacaatc gtattaatat ataagggttt tatatctatg tgtaggctgg    60
agctgcttcg                                                          70

<210> SEQ ID NO 48
<211> LENGTH: 70
<212> TYPE: DNA
<213> ORGANISM: Artificial Sequence
<220> FEATURE:
<223> OTHER INFORMATION: Oligonucleotide

<400> SEQUENCE: 48
taagcgtagc gccatcaggc atttacaact taaatcacac cctgcgccag catatgaata    60
tcctccttag                                                          70

<210> SEQ ID NO 49
<211> LENGTH: 21
<212> TYPE: DNA
<213> ORGANISM: Artificial Sequence
<220> FEATURE:
<223> OTHER INFORMATION: Oligonucleotide

<400> SEQUENCE: 49
ccttaacgtt attgtctctg c                                             21

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide

<400> SEQUENCE: 50
ggaggaagcc ccagagcagg                                               20

<210> SEQ ID NO 51
<211> LENGTH: 125
<212> TYPE: DNA
<213> ORGANISM: Artificial Sequence
<220> FEATURE:
<223> OTHER INFORMATION: Oligonucleotide

<400> SEQUENCE: 51
ggtaccggat ccgggcccga gctgttgaca attaatcatc cggctcgtat aatgtgtgga    60
attgtgagcg gataacaatt tacgtataag gaggtatatt atgaaagtta caaatcaaaa   120
agaac                                                              125

<210> SEQ ID NO 52
<211> LENGTH: 124
<212> TYPE: DNA
<213> ORGANISM: Artificial Sequence
<220> FEATURE:
<223> OTHER INFORMATION: Oligonucleotide

<400> SEQUENCE: 52
gagctcaagc ttaacagata aaacgaaagg cccagtcttt cgactgagcc tttcgtttta    60
tttgatgcct agggctagct ctagattaat taaaatgatt ttatatagat atccttaagt   120
tcac                                                               124
```

```
<210> SEQ ID NO 53
<211> LENGTH: 35
<212> TYPE: DNA
<213> ORGANISM: Artificial Sequence
<220> FEATURE:
<223> OTHER INFORMATION: Oligonucleotide

<400> SEQUENCE: 53
tctagaggat ccaagttcaa caggagagca ttatg                              35

<210> SEQ ID NO 54
<211> LENGTH: 44
<212> TYPE: DNA
<213> ORGANISM: Artificial Sequence
<220> FEATURE:
<223> OTHER INFORMATION: Oligonucleotide

<400> SEQUENCE: 54
ggatccgcta gccctaggta cgtactactc ttccatcgcc tggc                    44
```

METHOD FOR THE PREPARATION OF HYDROXY ACIDS

CROSS REFERENCE TO RELATED APPLICATIONS

This application is a §371 National Stage Application of PCT/EP2011/060836, filed Jun. 28, 2011, which claims priority to European Application No. 10305723.8, filed Jul. 2, 2010 and U.S. Provisional Application No. 61/361,125, filed Jul. 2, 2010.

BACKGROUND OF THE INVENTION

1. Field of the Invention

The present invention concerns a modified microorganism for the biological preparation of a hydroxy acid comprising culturing a microorganism genetically modified for the bioproduction of an aliphatic hydroxy acid of formula (I), wherein the microorganism comprises a metabolic pathway for the decarboxylation of a hydroxy-2-keto-aliphatic acid metabolite of formula (II) with two enzymes: an enzyme EA1 having a 2-keto acid decarboxylase activity and an enzyme EA2 having a hydroxy aldehyde dehydrogenase activity. The invention also concerns a new method for the fermentative production of an aliphatic hydroxy acid.

2. Description of Related Art

Fermentative production of hydroxy acids by culturing microorganism producing such hydroxy acids are known in the art, including fermentative production with microorganisms genetically modified for an improved production of the hydroxy acids.

Hydroxyacetate, also named glycolic acid, is the first member of the alpha-hydroxy acid family of carboxylic acids. Hydroxyacetate can form copolymers with other alpha-hydroxy acids. The polyester gradually hydrolyzes in aqueous environments at controllable rates. This property makes it useful in biomedical applications such as dissolvable sutures. Production of hydroxyacetate is described, inter alia, in the following document: WO2007/141316.

3-hydroxypropionate, also named 3-hydroxypropanoate or β-hydroxypropionate or 3-HP, is the three carbon member of the alpha-hydroxy acid family of carboxylic acids. Applications of 3-hydroxypropionate include the manufacture of absorbable prosthetic devices and surgical sutures, incorporation into beta-lactams, production of acrylic acid and malonic acid, formation of trifluoromethylated alcohols or diols (such as 1,3-propanediol), polyhydroxyalkanoates, and copolymers with lactic acid. Production of 3-hydroxypropionate is described, inter alia, in the following documents: WO 2001/16346, WO 2002/42418, WO 2003/062173, WO 2005/118719, WO 2006/022664, JP 2007/082476, WO 2008/027742, WO 2008/091627.

4-hydroxybutyrate, also named γ-hydroxybutyrate or GHB, is the four carbon member of the alpha-hydroxy acid family of carboxylic acids. 4-hydroxybutyrate is a naturally-occurring substance found in the central nervous system. 4-hydroxybutyrate finds some medical applications, to treat cataplexy and excessive daytime sleepiness in patients with narcolepsy, and as a general anesthetic. In addition to its medical uses, there are many commercial uses for 4-hydroxybutyrate, particularly its various polymers and copolymers. Further, there are several related chemicals that are also useful, 4-hydroxybutyraldehyde, lactone gamma butyrolactone (a common solvent and reagent in chemistry), or 1,4-butanediol (used as a solvent and in the manufacture of some types of plastics and fibers). Production of 4-hydroxybutyrate is described, inter alia, in the following documents: WO 2008/115840, WO 2009/061477.

There is an ongoing need for alternative solutions with modified microorganisms, to use various carbon sources and have potential improvement in the production of the hydroxy acids. These technical improvements may be the overall yield of product being produced based on the energy necessary for such production and eventually, the level of impurities and by-products to be specifically controlled for isolation of the product and its marketing and further use. The present invention relates to a new way of producing such hydroxy acids, describing new metabolic pathways from carbon sources to hydroxy acids.

SUMMARY

The present invention concerns a microorganism genetically modified for the bioproduction of a hydroxy acid of formula (I)

wherein the microorganism comprises a two-step metabolic pathway for the production of the said hydroxy acid from a hydroxy keto-acid of formula (II) through an intermediate hydroxy-aldehyde of formula (III)

$$HO-CH_2-(CH_2)_n-CO-COOH \xrightarrow{EA1}$$
$$(II)$$
$$HO-CH_2-(CH_2)_n-CHO$$
$$(III)$$
$$\downarrow EA2$$
$$HO-CH_2-(CH_2)_n-COOH$$
$$(I)$$

with n=0, 1, 2 or 3,
wherein
EA1 is an enzyme having a 2-keto-acid decarboxylase activity, and
EA2 is an enzyme having hydroxy aldehyde dehydrogenase activity.

The microorganism of the invention is generally selected among the group consisting of a bacterium, yeast or a fungus. Preferentially, the microorganism is selected among Enterobacteriaceae, Clostridiaceae, Bacillaceae, Streptomycetaceae and Corynebacteriaceae.

DETAILED DESCRIPTION OF A PREFERRED EMBODIMENT

Microorganisms

Figure 1:
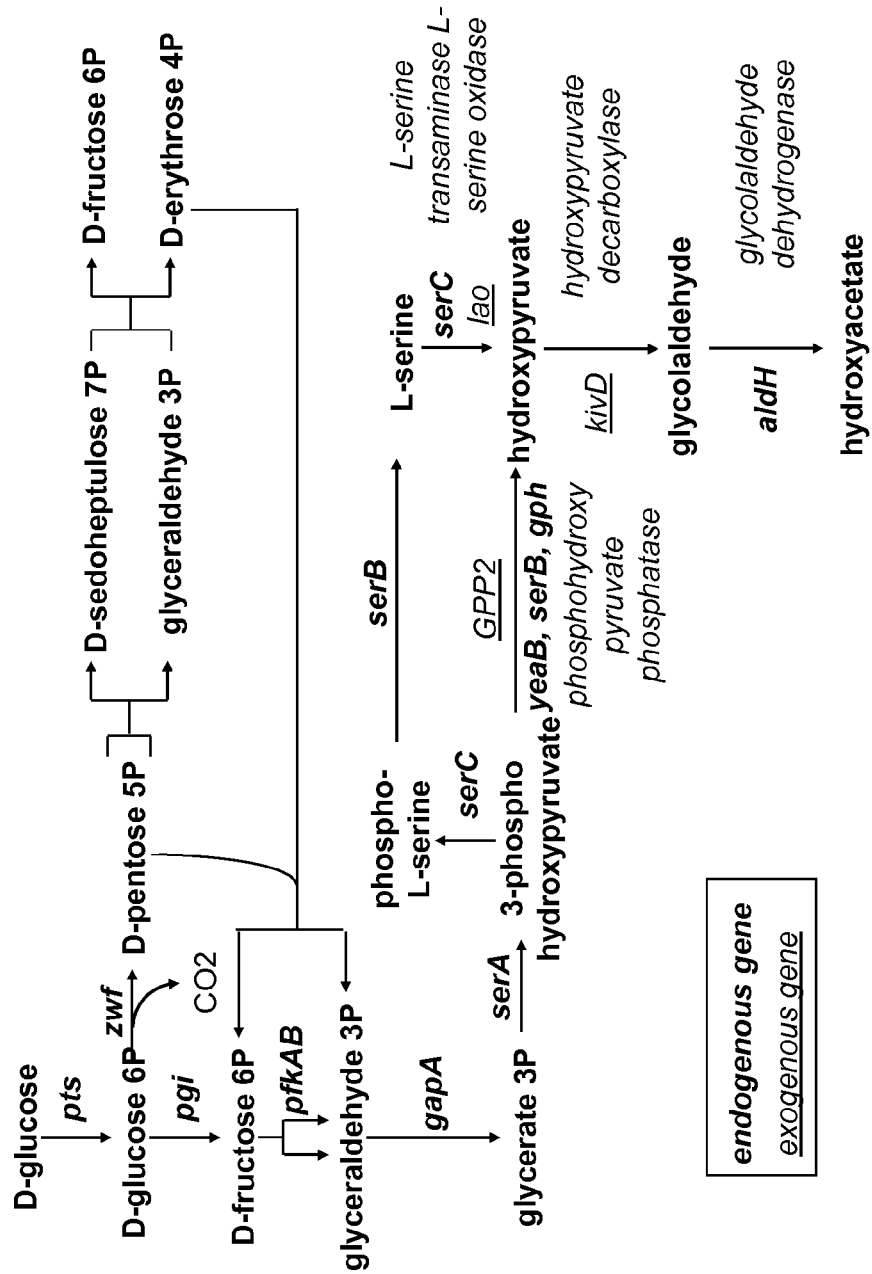
FIG. 1 represents the global biosynthesis pathway for the production of hydroxyacetate.

The microorganism of the invention is a microorganism being genetically modified or genetically engineered. It means, according to the usual meaning of these terms, that the microorganism of the invention is not found in nature and is modified either by introduction or by deletion of new genetic elements. It can also be transformed by forcing the development and evolution of new metabolic pathways in combining directed mutagenesis and evolution under specific selection pressure (see for instance WO 2004/076659).

According to the invention, the term "microorganism" designates a bacterium, yeast or a fungus. Preferentially, the microorganism is selected among Enterobacteriaceae, Clostridiaceae, Bacillaceae, Streptomycetaceae, Corynebacteriaceae and Saccharomycetaceae. More preferentially the microorganism is a species of *Escherichia, Clostridium, Bacillus, Klebsiella, Pantoea, Salmonella, Corynebacterium* or *Saccharomyces*. Even more preferentially the microorganism is either the species *Escherichia coli* or *Corynebacterium glutamicum* or *Clostridium acetobutylicum* or *Bacillus subtilis* or *Saccharomyces cerevisiae*.

A microorganism can express exogenous genes if these genes are introduced into the microorganism with all the elements allowing their expression in the host microorganism. Transforming microorganisms with exogenous DNA is a routine task for the man skilled in the art.

Exogenous genes can be integrated into the host genome, or be expressed extrachromosomally by plasmids or vectors. Different types of plasmids are known by the man skilled in the art, which differ with respect to their origin of replication and their copy number in the cell.

Important elements for controlling the expression of genes are promoters. In a preferred embodiment of the invention, genes may be expressed using promoters with different strength, which may be inducible. These promoters may be homologous or heterologous. The man skilled in the art knows how to choose the promoters that are the most convenient, for example promoters Ptrc, Ptac, Plac or the lambda promoter cI are widely used.

In specific embodiments, endogenous genes can also be modified to modulate their expression and/or activity, by introducing either mutations in the coding sequence to modify the gene product or by introducing heterologous sequences in addition or in replacement of the endogenous regulatory elements. Modulation of an endogenous gene can go both ways: upregulating and/or enhancing the activity of the gene product on the one hand, or down regulating and/or lowering the activity of the endogenous gene product on the other hand.

The term 'attenuation of a gene' according to the invention denotes the partial or complete suppression of the expression of a gene, which is then said to be 'attenuated'. This suppression of expression can be either an inhibition of the expression of the gene, a deletion of all or part of the promoter region necessary for the gene expression, a deletion in the coding region of the gene, or the replacement of the wild-type promoter by a weaker natural or synthetic promoter. Preferentially, the attenuation of a gene is essentially the complete deletion of that gene, which can be replaced by a selection marker gene that facilitates the identification, isolation and purification of the strains according to the invention. A gene is inactivated preferentially by the technique of homologous recombination (Datsenko, K. A. & Wanner, B. L. (2000) "One-step inactivation of chromosomal genes in *Escherichia coli* K-12 using PCR products". Proc. Natl. Acad. Sci. USA 97: 6640-6645).

In other embodiments of the invention, endogenous sequences may also be knocked out or deleted, to favour the new metabolic pathway.

All techniques for transforming the microorganisms, and regulatory elements used for enhancing production of the protein of the invention are well known in the art and available in the literature, including applicant's own patent applications on modification of biosynthesis pathways in various microorganisms, including WO 2008/052973, WO 2008/052595, WO 2008/040387, WO 2007/144346, WO 2007/141316, WO 2007/077041, WO 2007/017710, WO 2006/082254, WO 2006/082252, WO 2005/111202, WO 2005/073364, WO 2005/047498, WO 2004/076659, the content of which is incorporated herein by reference.

Genes and Enzymatic Activities

In the description of the present invention, enzymatic activities are also designated by reference to the genes coding for the enzymes having such activity. Except mentioned otherwise, genes and proteins are generally identified using the denominations of genes from *Escherichia coli*. However, use of these denominations has a more general meaning according to the invention and covers all the corresponding genes and proteins in other organisms, more particularly microorganisms, functional homologues, functional variants and functional fragments of said genes and proteins.

Using the references of the IUBMB Enzyme Nomenclature for known enzymatic activities, those skilled in the art are able to determine the same enzymatic activities in other organisms, bacterial strains, yeasts, fungi, etc. This routine work is advantageously done using consensus sequences that can be determined by carrying out sequence alignments with proteins derived from other microorganisms.

Methods for the determination of the percentage of homology between two protein sequences are known from the man skilled in the art. For example, it can be made after alignment of the sequences by using the software CLUSTALW available on the website www.ebi.ac.uk/clustalw/ with the default parameters indicated on the website. From the alignment, calculation of the percentage of identity can be made easily by recording the number of identical residues at the same position compared to the total number of residues. Alternatively, automatic calculation can be made by using for example the BLAST programs available on the website www.ncbi.nlm.nih.gov/BLAST/ with the default parameters indicated on the website.

PFAM (protein families database of alignments and hidden Markov models; www.sangerac.uk/Software/Pfam/) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; www.ncbi.nlm.nih.gov/COG/ are obtained by comparing protein sequences from 66 fully sequenced genomes representing 30 major phylogenic lines. Each COG is defined from at least three lines, which permits the identification of former conserved domains.

A protein sharing homology with the cited protein may be obtained from other microorganisms or may be a variant or a functional fragment of a natural protein.

The term "functional variant or functional fragment" means that the amino-acid sequence of the polypeptide may not be strictly limited to the sequence observed in nature, but may contain additional amino-acids. The term "functional fragment" means that the sequence of the polypeptide may include less amino-acid than the original sequence but still enough amino-acids to confer the enzymatic activity of the original sequence of reference. It is well known in the art that a polypeptide can be modified by substitution, insertion, deletion and/or addition of one or more amino-acids while retaining its enzymatic activity. For example, substitutions of one amino-acid at a given position by chemically equivalent amino-acids that do not affect the functional properties of a protein are common. For the purpose of the present invention, substitutions are defined as exchanges within one of the following groups:

Small aliphatic, non-polar or slightly polar residues: Ala, Ser, Thr, Pro, Gly
Polar, negatively charged residues and their amides: Asp, Asn, Glu, Gln
Polar, positively charged residues: H is, Arg, Lys
Large aliphatic, non-polar residues: Met, Leu, Ile, Val, Cys
Large aromatic residues: Phe, Tyr, Trp.

Changes that result in the substitution of one negatively charged residue for another (such as glutamic acid for aspartic acid) or one positively charged residue for another (such as lysine for arginine) can be expected to produce a functionally equivalent product.

The positions where the amino-acids are modified and the number of amino-acids subject to modification in the amino-acid sequence are not particularly limited. The man skilled in the art is able to recognize the modifications that can be introduced without affecting the activity of the protein. For example, modifications in the N- or C-terminal portion of a protein may be expected not to alter the activity of a protein under certain circumstances.

The terms "encoding" or "coding" refer to the process by which a polynucleotide, through the mechanisms of transcription and translation, produces an amino-acid sequence. This process is allowed by the genetic code, which is the relation between the sequence of bases in DNA and the sequence of amino-acids in proteins. One major feature of the genetic code is to be degenerate, meaning that one amino-acid can be coded by more than one triplet of bases (one "codon"). The direct consequence is that the same amino-acid sequence can be encoded by different polynucleotides. It is well known for the man skilled in the art that the use of codons can vary according to the organisms. Among the codons coding for the same amino-acid, some can be used preferentially by a given microorganism. It can thus be of interest to design a polynucleotide adapted to the codon usage of a particular microorganism in order to optimize the expression of the corresponding protein in this organism.

In some instance, genes or enzymes may be designated by the name of the activity. In some other instances, the designation by "activity" may mean a combination of two or more enzymes having in combination the desired activity. In such case, each enzyme in the combination may be encoded by distinct genes under control of different regulatory elements or a combination of genes under control of the same operon.

The enzyme EA1 having 2-keto acid decarboxylase activity is encoded by a gene chosen among a list of genes well known in the art, including but not limited to Pdc genes from various species, and more particularly the Pdc1, Pdc5, Pdc6, Aro10 and Thi3 genes from *Saccharomyces cerevisiae*, Kivd gene from *Lactococcus lactis*; Pdc gene from *Clostridium acetobutylicum*; Pdc2 and Pdc3 genes from *Arabidopsis thaliana*; Pdc1, Pdc2 and Aro10 genes from *Pichia stipitis*; Pdc gene from *Zymomonas mobilis*. The first subunit of the 2-ketoglutarate decarboxylase complex, coded by the gene sucA from *Escherichia coli*, also possesses 2-keto acid decarboxylase activity, as well as the enzyme coded by the gene dxs of *Escherichia coli*. Functional homologues, functional variants and functional fragments of said genes and proteins are indeed encompassed by the definition.

The enzyme EA2 having hydroxy aldehyde dehydrogenase activity is encoded by a gene selected from a list of genes well known in the art, including but not limited to the aldA, aldB, aldH, gabD genes from *Escherichia coli* or the ald4 gene from *Saccharomyces cerevisiae*. Functional homologues, functional variants and functional fragments of said genes and proteins are indeed encompassed by the definition.

Fermentative Production

The present invention also concerns the fermentative production of a hydroxy acid, comprising the steps of:
culturing a microorganism on an appropriate culture medium comprising a source of carbon and
recovering the hydroxy acid from the culture medium.

The fermentation is generally conducted in fermenters with an appropriate culture medium adapted to the microorganism being used, containing at least one simple carbon source, and if necessary co-substrates.

An 'appropriate culture medium' designates a medium (e.g., a sterile, liquid media) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like.

As an example of known culture mediums for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

As another example of culture medium for *C. glutamicum*, the culture medium can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583).

The term 'carbon source' or 'carbon substrate' or 'source of carbon' according to the present invention denotes any source of carbon that can be used by those skilled in the art to support the normal growth of a micro-organism, including hexoses (such as glucose, galactose or lactose), pentoses, monosaccharides, oligosaccharides, disaccharides (such as sucrose, cellobiose or maltose), molasses, starch or its derivatives, hemicelluloses and combinations thereof. An especially preferred simple carbon source is glucose. Another preferred simple carbon source is sucrose.

In some embodiments of the invention, the culture medium comprises a carbon source being a by-product of another process using biomass as starting material, or eventually, the product of mechanical and/or chemical and/or enzymatic, and in such instance in vitro or in vivo, degradation of biomass, such as degradation of cellulose.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

Recovering the hydroxy acid from the culture medium is a routine task for a man skilled in the art.

In one aspect of the invention, the recovered hydroxy acid is further purified.

Methods for recovering a hydroxy acid from a culture medium and its purification are known in the art and disclosed, inter alia in the following documents: EP 1416053 A1, WO 98/37050 A1, WO 2007/040458 A1, WO 2008/015885 A1, WO 2004/076398 A1, WO 2003/064366 A1, WO 2006/064611 A1, EP 0658628 A1, WO 93/00440 A1 and EP 0789023 A2.

Specific Embodiments

The invention relates to a microorganism genetically modified for the bioproduction of a hydroxy acid of formula (I) wherein the microorganism comprises a two-step metabolic pathway for the production of the said hydroxy acid from a hydroxy-keto acid of formula (II) through an intermediate hydroxyl-aldehyde of formula (III):

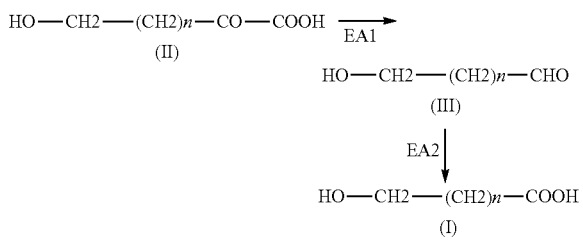

with n=0, 1, 2 or 3,
wherein
EA1 is an enzyme having a 2-ketoacid decarboxylase activity, and
EA2 is an enzyme having hydroxyl aldehyde dehydrogenase activity.

According to a first embodiment of the invention, the enzyme EA1 having a 2-keto acid decarboxylase activity is encoded by an endogenous gene. It is preferably selected among genes from *Saccharomyces cerevisiae* (Pdc1, Pdc5, Pdc6, Aro10, Thi3); *Lactococcus lactis* (Kivd); *Clostridium acetobutylicum* (Pdc); *Pichia stipitis* (Pdc1, Pdc2, Aro10); *Zymomonas mobilis* (Pdc); *Mycobacterium tuberculosis*. This microorganism having endogenous 2-keto acid decarboxylase activity can be further modified to enhance expression of the endogenous gene coding for the 2-keto acid decarboxylase.

According to another embodiment of the invention, the microorganism does not comprise an endogenous gene coding for the enzyme EA1 having a 2-keto acid decarboxylase. Such microorganism lacking endogenous 2-keto acid decarboxylase is preferably selected among *Escherichia coli* or *Corynebacterium glutamicum* or *Bacillus subtilis*. For such microorganisms, the microorganism of the invention comprises a heterologous gene coding for a 2-ketoacid decarboxylase. The heterologous gene can be chosen among the list previously presented, including Pdc genes from various species, and more particularly the Pdc1, Pdc5, Pdc6, Aro10 and Thi3 genes from *Saccharomyces cerevisiae*, Kivd gene from *Lactococcus lactis*; Pdc gene from *Clostridium acetobutylicum*; Pdc2 and Pdc3 genes from *Arabidopsis thaliana*; Pdc1, Pdc2 and Aro10 genes from *Pichia stipitis*; Pdc gene from *Zymomonas mobilis*.

According to another embodiment, the enzyme EA2 having hydroxyl aldehyde dehydrogenase activity is encoded by an endogenous gene. Preferentially, the microorganism is selected from one of the species of the following genera: an *Escherichia*, an *Aerobacter*, an *Agrobacterium*, an *Alcaligenes*, an *Arthrobacter*, a *Bacillus*, a *Corynebacterium*, a *Flavobacterium*, a *Klebsiella*, a *Micrococcus*, a *Protaminobacter*, a *Proteus*, a *Pseudomonas*, a *Salmonella*, a *Sarcina*, a *Staphylococcus*, a *Shigella*, an *Erwinia*, and a *Neisseria*, and in more detail, the species *Escherichia coli*, *Aerobacter aerogenes*, *Agrobacterium radiobacter*, *Agrobacterium tumefaciens*, *Alcaligenes viscolactis*, *Arthrobacter simplex*, *Bacillus lichenifonnis*, *Bacillus megaterium*, *Bacillus subtilis*, *Corynebacterium equi*, *Flavobacterium* sp., *Klebsiella pneumonia* (locus name AB 106869), *Micrococcus glutamicus*, *Protaminobacter alboflavus*, *Proteus vulgaris*, *Pseudomonas fluorescens*, *Salmonella typhimurium*, *Sarcina lutea*, *Staphylococcus aureus*, *Shigella flexneri* (locus name AE016982), *Erwinia carotovora* (locus name BX950851), *Neisseria meningitides* (locus name AL162753), *Neisseria gonorrhoeae* (locus name AE004969). It is preferably selected among *Escherichia coli*, and genes encoding for EA2 are more particularly the genes aldA, aldB, aldH, gabD coding for hydroxy aldehyde dehydrogenase activity; and all organisms having at least one enzyme having hydroxy aldehyde dehydrogenase activity. This microorganism having endogenous hydroxy aldehyde dehydrogenase activity can be further modified to enhance expression of the endogenous gene coding for the hydroxy aldehyde dehydrogenase.

According to another embodiment, the enzyme EA2 having hydroxyl aldehyde dehydrogenase activity is encoded by an heterologous gene. Genes can be chosen in the list presented below, including the aldA, aldB, aldH, gabD genes from *Escherichia coli* or the ald4 gene from *Saccharomyces cerevisiae*.

According to another embodiment of the invention, the production of hydroxy-2-keto-aliphatic acid metabolite of formula (II) is improved in the microorganism.

In a specific embodiment of the invention, in the microorganism, endogenous genes encoding for hydroxy aldehyde reductase activity have been deleted.

The hydroxy acid of formula (I) produced with the microorganims of the invention is an aliphatic hydroxy acid having a linear or branched alkyle chain comprising from 2 to 6 carbon atoms, preferably 2, 3 or 4 carbon atoms.

In a preferred embodiment, the hydroxy acid of formula (I) is hydroxyacetate and the hydroxy-2-keto-aliphatic acid metabolite of formula (II) is hydroxypyruvate.

In another preferred embodiment, the hydroxy acid of formula (I) is 3-hydroxypropionate and the hydroxy-2-keto-acid metabolite of formula (II) is 4-hydroxy-2-ketobutyrate.

In another preferred embodiment, the hydroxy acid of formula (I) is 4-hydroxybutyrate and the hydroxy-2-keto-acid metabolite of formula (II) is 5-hydroxy-2-ketopentanoate.

The microorganism according to the invention is selected among bacterium, yeast and fungus. Preferentially, the microorganism is a bacterium that is selected among Enterobacteriaceae, Clostridiaceae, Bacillaceae, Streptomycetaceae and Corynebacteriaceae.

The microorganisms are modified both to favor the production of the hydroxy-2-keto-acid metabolite of formula (II) and the transformation into the corresponding hydroxy acid of the product obtained from the decarboxylation step of the same hydroxy-2-keto-acid metabolite.

The description below is made by reference to *E. coli*, which microorganism is lacking endogenous 2-keto acid decarboxylase activity. Therefore, a heterologous gene coding for said activity is introduced into the microorganism.

Modifications of the microorganism to optimise the pathway for producing the hydroxy-2-keto-acid metabolite and to transform the product obtained from the decarboxylation step of the same hydroxy-2-keto-acid metabolite into the hydroxy acid is also made based on the known metabolic pathways and endogenous genes of *E. coli*. However, the man skilled in the art can use similar strategies to introduce or delete corresponding genes in other microorganisms with known genes and pathways.

The present invention also concerns a method for the bioproduction of a hydroxy acid of formula (I), comprising the steps of:
culturing a microorganism of the invention as described above and below on an appropriate culture medium comprising a source of carbon and
recovering the hydroxy acid from the culture medium.

According to preferred embodiment of the invention, the hydroxy acid is further purified.

The source of carbon is selected among hexoses, pentoses, monosaccharides, disaccharides, oligosaccharides, molasses, starch, hemicelluloses, glycerol and combinations thereof.

I. Preparation of Hydroxyacetate of Formula (I) with n=0

The biosynthesis pathway for the production of hydroxyacetate according to the invention comprises three enzymatic reactions starting with transformation of the 3-phosphohydroxypyruvate precursor (precursor for serine). First a phosphatase activity allows conversion of phosphohydroxypyruvate into hydroxypyruvate of formula (II) with n=0.

Hydroxypyruvate is then transformed into glycolaldehyde of formula (III) with a 2-keto acid decarboxylase activity (EA1). A hydroxy aldehyde dehydrogenase activity (EA2) allows finally the conversion of glycolaldehyde into hydroxyacetate of formula (I).

Another pathway for the production of hydroxyacetate starts from the L-serine precursor. First a transaminase or an amino acid oxidase activity allows conversion of serine into hydroxypyruvate. The next two steps are similar with the first pathway described above.

The global biosynthesis pathway is represented in FIG. 1.

The present invention provides a method for the fermentative production of hydroxyacetate, its derivatives or precursors, comprising: culturing a bacterium in an appropriate culture medium comprising a source of carbon and recovering hydroxyacetate from the culture medium.

The method is performed with a bacterium which contains at least one gene encoding a polypeptide with 2-keto acid decarboxylase activity (enzyme EA1) and one gene encoding a polypeptide with hydroxy aldehyde dehydrogenase activity (enzyme EA2). Those genes can be exogenous or endogenous, and can be expressed chromosomally or extrachromosomally.

In a further embodiment of the invention, the method is performed with a bacterium in which the availability of the intermediate product 3-phosphoglycerate is increased. Preferably, this result is achieved by attenuating the level of expression of genes coding for phosphoglycerate mutases, in particular one or both of gpmA and pgmI genes. This can be done by replacing the wild-type promoter of these genes by a lower strength promoter, or by the use of an element destabilizing the corresponding messenger RNA or the protein. If needed, complete attenuation of the genes can also be achieved by a deletion of the corresponding DNA sequences. The invention is also related to the bacterium used in this particular embodiment of the invention, i.e. a bacterium presenting an increased availability of 3-phosphoglycerate, in particular a bacterium in which the level of expression of the genes coding for phosphoglycerate mutases is attenuated, preferably the level of expression of one or both gpmA and pgmI genes.

In another embodiment, the method is performed with a bacterium in which the flux in the serine biosynthesis pathway is stimulated; this result can be achieved by increasing the level of expression of the 3-Phosphoglycerate dehydrogenase and/or phosphoserine aminotransferase, encoded by the serA and serC gene, respectively. Increasing the level of expression of the 3-Phosphoglycerate dehydrogenase and/or phosphoserine aminotransferase can be accomplished by introducing artificial promoters that drive the expression of the serA and/or serC gene, by increasing the number of copies in the cell or by introducing mutations into the serA and/or serC gene that increase the activity of the corresponding proteins. The expression of the serA gene can also be increased by replacing the wild type lrp gene (encoding the leucine-responsive regulatory protein) by an lrp mutated allele (such as the lrp-1 allele corresponding to a GLU114ASP substitution in the lrp protein) leading to the constitutive activation of the transcription of the serA gene. The invention is also related to the bacterium used in this particular embodiment of the invention.

In a particular embodiment of the invention mutations can be introduced into the serA gene that reduce the SerA protein sensitivity to the feed-back inhibitor serine (feed-back desensitized alleles) and thus permit an increased activity in the presence of serine. Examples of desensitized alleles, i.e. feed-back insensitive alleles, have been described in EP 0 931 833 (Ajinomoto) or EP 0 620 853 (Wacker).

In another embodiment, the method is performed with a bacterium in which the production of hydroxypyruvate of formula (II) is improved. This result can be achieved by increasing the level of expression of the serine transaminase or the serine oxidase (for the pathway starting from serine as precursor), or by increasing the 3-phosphohydroxypyruvate phosphatase. Increasing the level of expression of the 3-phosphohydroxypyruvate phosphatase can be accomplished by introducing artificial promoters that drive the expression of the yeaB gene, by increasing the number of copies in the cell or by introducing mutations into the yeaB gene that increase the activity of the corresponding proteins. The invention is also related to the bacterium used in this particular embodiment of the invention.

In a further embodiment of the invention, the bacterium is modified to present an attenuated level of serine conversion to other compounds than hydroxyacetate; this result may be achieved by attenuating the level of serine consuming enzymes like serine deaminases (encoded by sdaA, sdaB and tdcG), serine transacetylase (encoded by cysE), tryptophan synthase (encoded by trpAB) or serine hydroxymethyltransferase (encoded by glyA). Attenuation of these genes can be done by replacing the natural promoter by a lower strength promoter or by elements destabilizing the corresponding messenger RNA or the protein. If needed, complete attenuation of the gene can also be achieved by a deletion of the corresponding DNA sequence. The invention is also related to the bacterium used in this particular embodiment of the invention.

In a further embodiment of the invention, the bacterium is modified to present an attenuated level of hydroxypyruvate conversion to other compounds than hydroxyacetate; this result may be achieved by attenuating the level of hydroxypyruvate consuming enzymes like hydroxypyruvate reductase (encoded by ghrA) or hydroxypyruvate isomerase (encoded by hyi). Attenuation of these genes can be done by replacing the natural promoter by a lower strength promoter or by element destabilizing the corresponding messenger RNA or the protein. If needed, complete attenuation of the gene can also be achieved by a deletion of the corresponding DNA sequence. The invention is also related to the bacterium used in this particular embodiment of the invention.

In a further embodiment of the invention, the bacterium is modified to present an attenuated level of glycolaldehyde conversion to other compounds than hydroxyacetate; this result may be achieved by attenuating the level of glycolaldehyde consuming enzymes like hydroxythreonine aldolase (encoded by ltaE) or glycolaldehyde reductase (encoded by yqhD, fucO, dkgA, dkgB). Attenuation of these genes can be done by replacing the natural promoter by a lower strength promoter or by element destabilizing the corresponding messenger RNA or the protein. If needed, complete attenuation of the gene can also be achieved by a deletion of the corresponding DNA sequence. The invention is also related to the bacterium used in this particular embodiment of the invention.

In one aspect of the invention, the efficiency of the sugar import is increased, either by using a sugar import independent of phosphoenolpyruvate (PEP) like the one encoded by galP, or by providing more phosphoenolpyruvate (PEP) to the sugar-phosphotransferase system. Various means exist that may be used to increase the availability of PEP in a strain of microorganism. In particular, a mean is to attenuate the reaction PEP→pyruvate. Preferentially, at least one gene selected among pykA and pykF, coding for the pyruvate kinase enzyme, is attenuated in said strain to obtain this result. Another way to increase the availability of PEP is to favour the reaction pyruvate→PEP, catalysed by the phosphoenolpyruvate synthase by increasing the activity of this enzyme. This enzyme is encoded by the ppsA gene. Therefore, preferentially in the microorganism, the expression of the ppsA gene is preferentially increased. Both modifications can be present in the microorganism simultaneously.

II. Preparation of 3-Hydroxypropionate of Formula (I) with n=1

The biosynthesis pathway for the production of 3-hydroxypropionate according to the invention comprises three enzymatic reactions starting with transformation of the L-homoserine precursor (obtained from L-aspartate). First a homoserine transaminase or a homoserine oxidase activity allows conversion of L-homoserine into 4-hydroxy-2-ketobutyrate of formula (II) with n=1. Secondly, the enzyme EA1 having 2-keto acid decarboxylase activity catalyzes the conversion of 4-hydroxy-2-ketobutyrate into 3-hydroxypropionaldehyde of formula (III). 3-hydroxypropionaldehyde is then converted into 3-hydroxypropionate with the enzyme EA2 having hydroxy aldehyde dehydrogenase activity.

Figure 2:
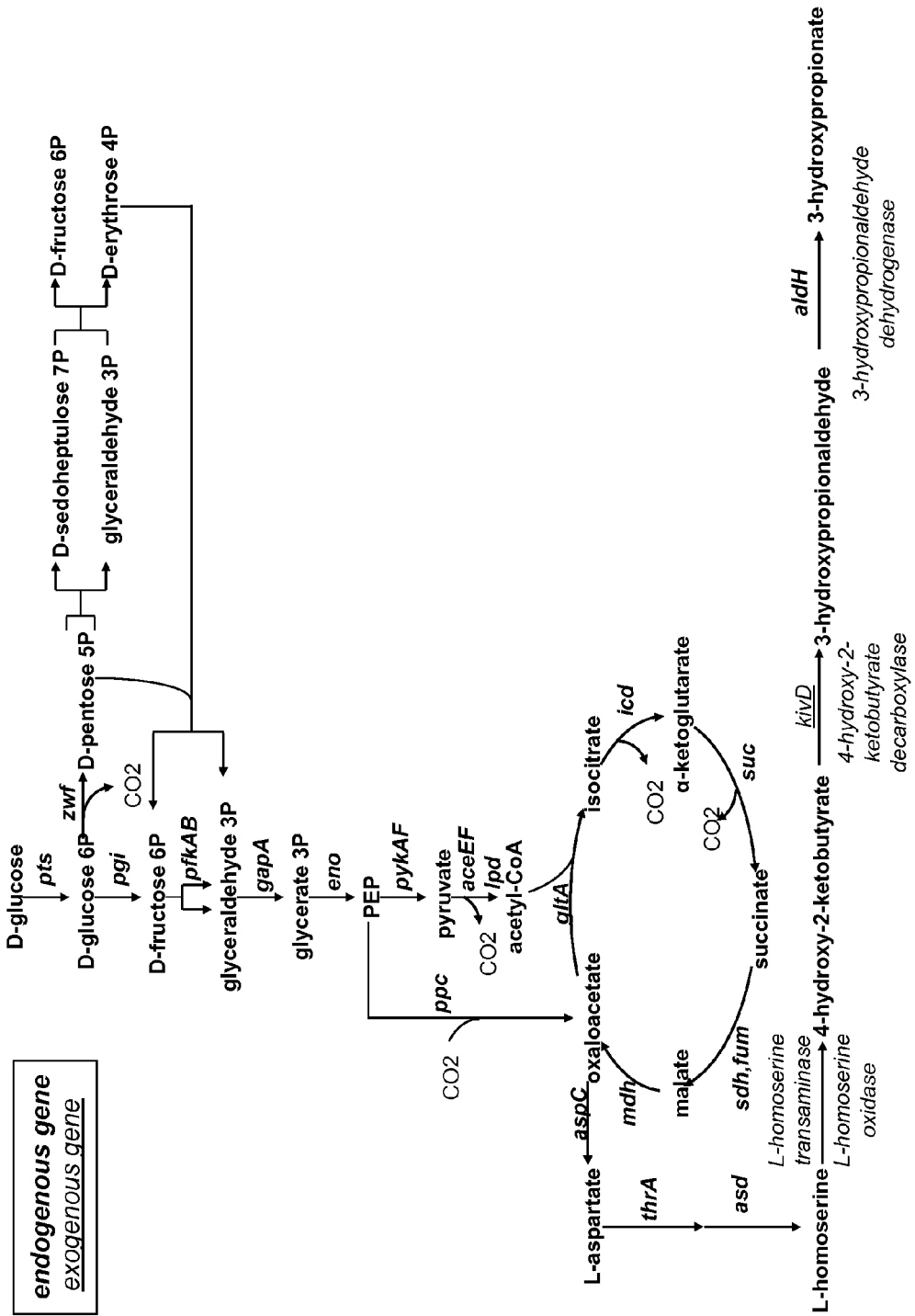
FIG. 2 represents the global biosynthesis pathway for the production of 3-hydroxypropionate.

The global biosynthesis pathway is represented in FIG. 2.

The method is performed with a bacterium that contains at least one gene encoding a polypeptide with 2-keto acid decarboxylase activity and one gene encoding a polypeptide with hydroxy aldehyde dehydrogenase activity. Those genes can be exogenous or endogenous, and can be expressed chromosomally or extrachromosomally.

In a specific embodiment of the invention, the method is performed with a bacterium in which the flux in the oxaloacetate biosynthesis pathway is stimulated; this result can be achieved by increasing the level of expression of the phosphoenolpyruvate carboxylase, encoded by the ppc gene. Increasing the level of expression of the phosphoenolpyruvate carboxylase can be accomplished by introducing artificial promoters that drive the expression of the ppc gene, by increasing the number of copies in the cell or by introducing mutations into the ppc gene that increase the activity of the corresponding protein. Increase of the oxaloacetate pool can also be achieved by increasing the level of expression of the exogenous pyruvate carboxylase, encoded by the pyc gene of *Rhizobium etli* or *Corynebacterium glutamicum*. Increasing the level of expression of the pyruvate carboxylase can be accomplished by overexpressing these genes, chromosomally or extrachromosomally. Specifically in anaerobic conditions, increase of the oxaloacetate pool can also be achieved by increasing the level of expression of the phosphoenolpyruvate carboxykinase, encoded by the pckA gene. Increasing the level of expression of the pyruvate carboxylase can be accomplished by introducing artificial promoters that drive the expression of the pckA gene, by increasing the number of copies in the cell or by introducing mutations into the pckA gene that increase the activity of the corresponding protein. Availability of the intermediate product oxaloacetate can also be increased by attenuating the level of expression of genes coding for phosphoenolpyruvate carboxykinase and/or malic enzymes, encoded by the pckA and/or sfcA or maeB genes, respectively. This can be done by replacing the wild-type promoter of these genes by a lower strength promoter, or by use of an element destabilizing the corresponding messenger RNA or the protein. If needed, complete attenuation of the genes can also be achieved by a deletion of the corresponding DNA sequences. The invention is also related to the bacterium used in this particular embodiment of the invention, i.e. a bacterium presenting an increased availability of the 2-ketoglutarate.

In another embodiment, the method is performed with a bacterium in which the flux in the homoserine biosynthesis pathway is stimulated; this result can be achieved by increasing the level of expression of the aspartokinase and homoserine dehydrogenase and/or aspartate semialdehyde dehydrogenase, encoded by the thrA/metL and asd gene, respectively. Increasing the level of expression of the aspartokinase and homoserine dehydrogenase and/or aspartate semialdehyde dehydrogenase can be accomplished by introducing artificial promoters that drive the expression of the thrA or metL and/or asd gene, by increasing the number of copies in the cell or by introducing mutations into the thrA and/or asd gene that increase the activity of the corresponding protein. The invention is also related to the bacterium used in this particular embodiment of the invention.

In a particular embodiment of the invention mutations can be introduced into the thrA gene that reduce its sensitivity to the feed-back inhibitor threonine (feed-back desensitized alleles) and thus permit an increased activity in the presence of threonine.

In another embodiment, the method is performed with a bacterium wherein the production of 4-hydroxy-2-ketobutyrate of formula (II) is improved. This result can be achieved by increasing the level of expression of the homoserine transaminase or the homoserine oxidase. The invention is also related to the bacterium used in this particular embodiment of the invention.

In a further embodiment of the invention, the bacterium is modified to present an attenuated level of homoserine conversion to other compounds than 3-hydroxypropionate; this result may be achieved by attenuating the level of homoserine consuming enzymes like homoserine kinase and threonine synthase (encoded by thrB and thrC), homoserine O-transsuccinylase (encoded by metA). Attenuation of these genes can be done by replacing the natural promoter by a lower strength promoter or by element destabilizing the corresponding messenger RNA or the protein. If needed, complete attenuation of the gene can also be achieved by a deletion of the corresponding DNA sequence. The invention is also related to the bacterium used in this particular embodiment of the invention.

In a further embodiment of the invention, the bacterium is modified to present an attenuated level of homoserine precursors conversion to other compounds than 3-hydroxypropionate; this result may be achieved by attenuating the level of dihydrodipicolinate synthase (encoded by dapA). Attenuation of this gene can be done by replacing the natural promoter by a lower strength promoter or by element destabilizing the corresponding messenger RNA or the protein. If needed, complete attenuation of the gene can also be achieved by a deletion of the corresponding DNA sequence. The invention is also related to the bacterium used in this particular embodiment of the invention.

In a further embodiment of the invention, the bacterium is modified to present an attenuated level of 3-hydroxypropionaldehyde conversion to other compounds than 3-hydroxypropionate; this result may be achieved by attenuating the level of 3-hydroxypropionaldehyde consuming enzymes like 3-hydroxypropionaldehyde reductase (encoded by yqhD, fucO, dkgA, dkgB). Attenuation of these genes can be done by replacing the natural promoter by a lower strength promoter or by elements destabilizing the corresponding messenger RNA or the protein. If needed, complete attenuation of the gene can also be achieved by a deletion of the corresponding DNA sequence. The invention is also related to the bacterium used in this particular embodiment of the invention.

In one aspect of the invention, the efficiency of the sugar import is increased, either by using a sugar import independent of phosphoenolpyruvate (PEP) like the one encoded by galP, or by providing more phosphoenolpyruvate (PEP) to the sugar-phosphotransferase system. Various means exist that may be used to increase the availability of PEP in a strain of microorganism. In particular, a mean is to attenuate the reaction PEP→pyruvate. Preferentially, at least one gene selected among pykA and pykF, coding for the pyruvate kinase enzyme, is attenuated in said strain to obtain this result. Another way to increase the availability of PEP is to favour the reaction pyruvate→>PEP, catalysed by the phosphoenolpyruvate synthase by increasing the activity of this enzyme. This enzyme is encoded by the ppsA gene. Therefore, preferentially in the microorganism, the expression of the ppsA gene is preferentially increased. Both modifications can be present in the microorganism simultaneously.

III. Preparation of 4-Hydroxybutyrate of Formula (IA) with n=2

The biosynthesis pathway for the production of 4-hydroxybutyrate according to the invention comprises five enzymatic reactions starting with transformation of the 2-oxoglutarate precursor (precursor of the Krebs cycle).

A first activity 4-oxoglutaryl-CoA synthetase allows conversion of 2-oxoglutarate into 4-oxoglutaryl-CoA. This compound is then converted into 5-hydroxy-2-ketopentanoate of formula (II) with the combinations of two activities, first aldehyde dehydrogenase then second alcohol dehydrogenase both encoded by the gene adhE of *Escherichia coli*. The enzyme EA1 with activity 2-keto acid decarboxylase allows conversion of 5-hydroxy-2-oxopentanoate into 4-hydroxybutyraldehyde of formula (III), further converted into 4-hydroxybutyrate with the enzyme EA2 having hydroxy aldehyde dehydrogenase activity.

Figure 3:
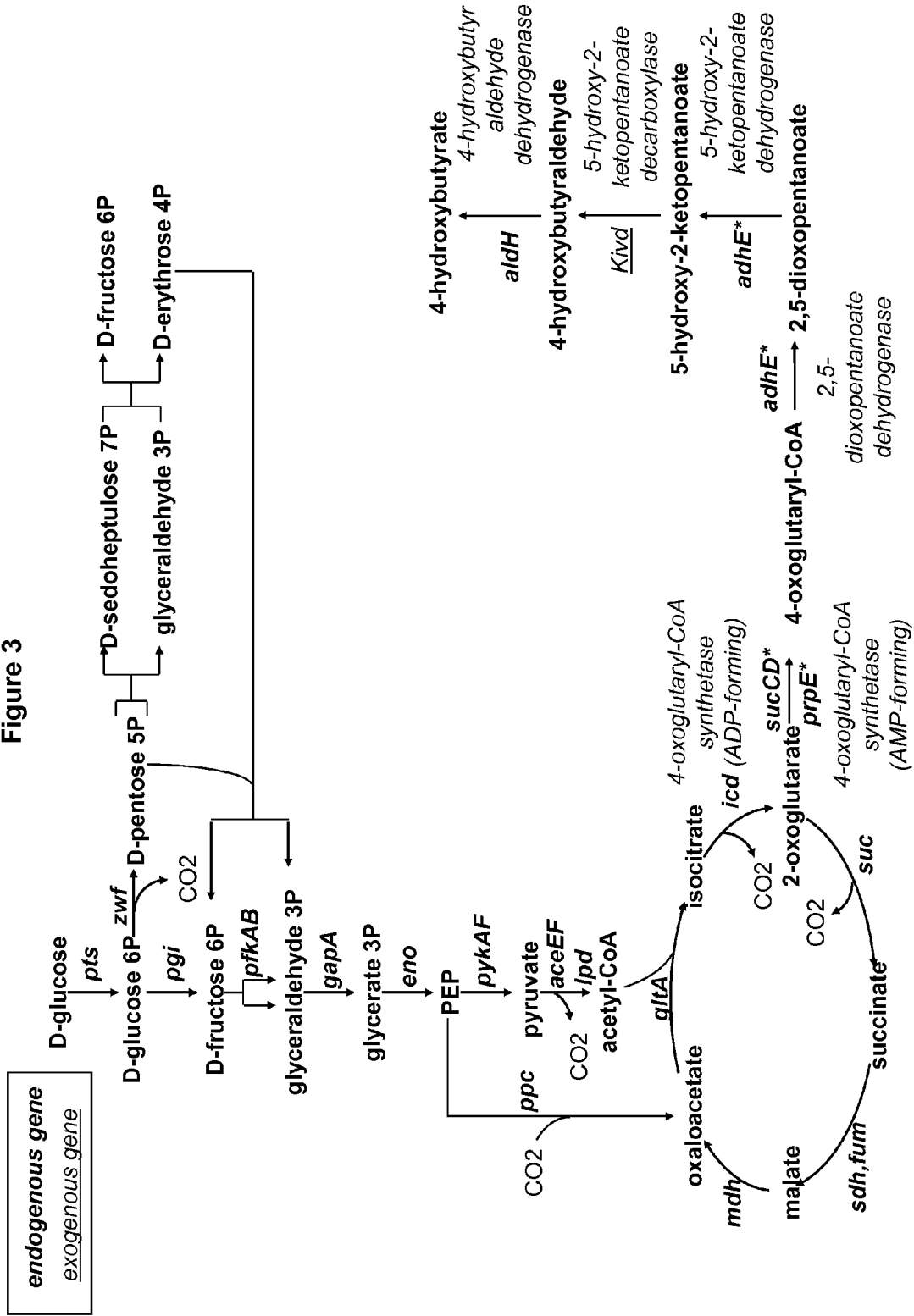
FIG. 3 represents the global biosynthesis pathway for the production of 4-hydroxybutyrate.

The global biosynthesis pathway is represented in FIG. 3.

The present invention provides a method for the fermentative production of 4-hydroxybutyrate of formula (I) with n=2, its derivatives or precursors, comprising: culturing a bacterium in an appropriate culture medium comprising a source of carbon and recovering 4-hydroxybutyrate from the culture medium.

In a preferred embodiment, the method is performed with a bacterium that contains at least one gene encoding a polypeptide with 2-keto acid decarboxylase activity and one gene encoding a polypeptide with hydroxy aldehyde dehydrogenase activity. Those genes can be exogenous or endogenous, and can be expressed chromosomally or extrachromosomally.

In another embodiment, the method is performed with a bacterium in which the flux in the oxaloacetate biosynthesis pathway is stimulated (entry of the Krebs cycle); this result can be achieved by increasing the level of expression of the phosphoenolpyruvate carboxylase, encoded by the ppc gene. Increasing the level of expression of the phosphoenolpyruvate carboxylase can be accomplished by introducing artificial promoters that drive the expression of the ppc gene, by increasing the number of copies in the cell or by introducing mutations into the ppc gene that increase the activity of the corresponding protein. Increase of the oxaloacetate pool can also be achieved by increasing the level of expression of the exogenous pyruvate carboxylase, encoded by the pyc gene of *Rhizobium etli* or *Corynebacterium glutamicum*. Increasing the level of expression of the pyruvate carboxylase can be accomplished by overexpressing these genes, chromosomally or extrachromosomally. Specifically in anaerobic conditions, increase of the oxaloacetate pool can also be achieved by increasing the level of expression of the phosphoenolpyruvate carboxykinase, encoded by the pckA gene. Increasing the level of expression of the pyruvate carboxylase can be accomplished by introducing artificial promoters that drive the expression of the pckA gene, by increasing the number of copies in the cell or by introducing mutations into the pckA gene that increase the activity of the corresponding protein. Availability of the intermediate product oxaloacetate can also be increased by attenuating the level of expression of genes coding for phosphoenolpyruvate carboxykinase and/or malic enzymes, encoded by the pckA and/or sfcA or maeB genes, respectively. This can be done by replacing the wild-type promoter of these genes by a lower strength promoter, or by use of an element destabilizing the corresponding messenger RNA or the protein. If needed, complete attenuation of the genes can also be achieved by a deletion of the corresponding DNA sequences. The invention is also related to the bacterium used in this particular embodiment of the invention, i.e. a bacterium presenting an increased availability of the 2-ketoglutarate.

In another embodiment, the method is performed with a bacterium whose flux in the 2-ketoglutarate biosynthesis pathway is stimulated; this result can be achieved by increasing the level of expression of the citrate synthase and/or isocitrate dehydrogenase, encoded by the gltA and icd gene, respectively. Increasing the level of expression of the citrate synthase and/or isocitrate dehydrogenase can be accomplished by introducing artificial promoters that drive the expression of the gltA and/or icd gene, by increasing the number of copies in the cell or by introducing mutations into the gltA and/or icd gene that increase the activity of the corresponding protein. Isocitrate dehydrogenase activity is modulated by its phosphorylation or dephosphorylation catalyzed by AceK. Phosphorylation reduces the activity of Icd and dephosphorylation reactivates the Icd enzyme. Since the activity of the protein Icd is reduced by phosphorylation, it may also be controlled by introducing mutant aceK genes that have reduced kinase activity or increased phosphatase activity compared to the wild type AceK enzyme. Level of AceK can also be decreased by attenuating the level of expression of the aceK gene. This can be done by replacing the wild-type promoter of this gene by a lower strength promoter, or by use of an element destabilizing the corresponding messenger RNA or the protein. If needed, complete attenuation of the gene can also be achieved by a deletion of the corresponding DNA sequence. Availability of the intermediate product 2-ketoglutarate can also be increased by attenuating the level of expression of genes coding for 2-ketoglutarate decarboxylase or succinyl-CoA synthetase and/or isocitrate lyase or malate synthase, encoded by the sucAB or sucCD and/or aceA or aceB genes, respectively. This can be done by replacing the wild-type promoter of these genes by a lower strength promoter, or by use of an element destabilizing the corresponding messenger RNA or the protein. Increase of the flux in the Krebs cycle can also be obtained by alleviating the repression on the Krebs cycle mediated by the global regulator ArcA (encoded by the arcA gene). The invention is also related to the bacterium used in this particular embodiment of the invention, i.e. a bacterium presenting an increased availability of the 2-ketoglutarate.

In another embodiment, the method is performed with a bacterium wherein the production of 5-hydroxy-2-ketopentanoate of formula (II) is improved. This result can be achieved by increasing the level of expression of the 4-oxoglutaryl-CoA synthetase (AMP-forming like the one coded by prpE gene, or ADP-forming like the one coded by sucC and sucD genes) and/or the aldehyde reductase/alcohol dehydrogenase coded by the adhE gene. The invention is also related to the bacterium used in this particular embodiment of the invention.

In a further embodiment of the invention, the bacterium is modified to present an attenuated level of 2-ketoglutarate conversion to other compounds than 4-hydroxybutyrate; this result may be achieved by attenuating the level of 2-ketoglutarate consuming enzymes like glutamate dehydrogenase or glutamate synthase (encoded by gdhA and gltB). Attenuation of these genes can be accomplished by replacing the natural promoter by a lower strength promoter or by elements destabilizing the corresponding messenger RNA or the protein. If needed, complete attenuation of the gene can also be achieved by a deletion of the corresponding DNA sequence. The invention is also related to the bacterium used in this particular embodiment of the invention.

In a further embodiment of the invention, the bacterium is modified to present an attenuated level of 4-hydroxybutyraldehyde conversion to other compounds than 4-hydroxybutyrate; this result may be achieved by attenuating the level of 4-hydroxybutyraldehyde consuming enzymes like 4-hydroxybutyraldehyde reductase (encoded by yqhD, fucO, dkgA, dkgB). Attenuation of these genes can be accomplished by replacing the natural promoter by a lower strength promoter or by element destabilizing the corresponding messenger RNA or the protein. If needed, complete attenuation of the gene can also be achieved by a deletion of the corresponding DNA sequence. The invention is also related to the bacterium used in this particular embodiment of the invention.

Drawings

FIG. 1: biosynthesis pathway of hydroxyacetate
FIG. 2: biosyntheis pathway of 3-hydroxypropionate
FIG. 3: biosyntheis pathway of 4-hydroxybutyrate Before describing the present invention in detail, it is to be understood that this invention is not limited to particularly exemplified methods and may, of course, vary. In particular, examples show modified *Escherichia coli* strains, but these modifications can easily be performed on other microorganisms of the same family.

*Escherichia coli* belongs to the Enterobacteriaceae family, that comprises members that are Gram-negative, rod-shaped, non-spore forming and are typically 1-5 µm in length. Most members have flagella used to move about, but a few genera are non-motile. Many members of this family are a normal part of the gut flora found in the intestines of humans and other animals, while others are found in water or soil, or are parasites on a variety of different animals and plants. *Escherichia coli* is one of the most important model organisms, but we can also cite as important members of the Enterobacteriaceae family: *Klebsiella*, in particular *Klebsiella pneumoniae*, and *Salmonella*.

EXAMPLE 1

Simulation of maximum yields for Hydroxyacetate, 3-hydroxypropionate and 4-hydroxybutyrate production 1.1 Parameters used for simulations Simulations have been performed with the METEX proprietary software METOPT™. A simplified metabolic network of *E. coli* has been used including a central metabolic network, metabolic pathways for all biomass precursors and specific production pathways as described above. A classical biomass composition for *E. coli* has been used. For each specific hydroxy acid, two simulations have been performed. The first one to calculate a theoretical maximum yield (taking into account only stoichiometry of the model, with no growth and no maintenance energy). The second one to calculate a practical maximum yield, taking into account a growth rate of $0.1\ h^{-1}$ and maintenance energy of 5 $mmol_{ATP} \cdot g_{DW}^{-1} \cdot h^{-1}$. All simulations have been performed with a specific uptake rate of glucose of 3 mmol $g_{DW}^{-1} \cdot h^{-1}$. All simulations have been performed in aerobic conditions.

1.2 Simulations Results

|  | Hydroxyacetate | 3-hydroxypropionate | 4-hydroxybutyrate |
|---|---|---|---|
| Maximum theoretical yield (g/g) | 0.84 | 0.75 | 0.58 |
| Maximum practical yield (g/g) | 0.62 | 0.47 | 0.43 |

EXAMPLE 2

Demonstration of the Hydroxy Keto-Acid Decarboxylase Activity Encoded by the Gene Kivd of *Lactococcus lactis*

2.1 Construction of Strain for Kivd Characterisation: BL21 (pPal7-kivDll)

To characterise the KivD protein, the corresponding gene was expressed from the expression vector pPAL7 (Bio-rad).

For this purpose, the kivD gene was amplified from the *Lactococcus lactis* genome using the oligonucleotides pPAL7-kivDll F and pPAL7-kivDll R. The PCR product was restricted using enzymes HindIII and EcoRI and cloned into the vector pPAL7 restricted by the same restriction enzymes. The resulting vector was named pPAL7-kivDll.

pPAL7-kivDll F (SEQ ID NO 1):
ccc<u>AAGCTT</u>gACTTCTATGTATACCGTGGGTGATTATC with
a region (italic case) homologous to the sequence of the synthetic gene of the *Lactococcus lactis* kivD gene,
  a region (bold case) harbouring the nucleotides necessary to generate tag-free protein containing a short N-terminal amino acid extension to favour the purification
  a region (underlined case) harbouring the HindIII restriction site pPAL7-kivDll R (SEQ ID NO 2):
g<u>GAATTC</u>TTAGCTTTTATTCTGTTCGGCGAACAG with
a region (italic case) homologous to the sequence of the synthetic gene of the *Lactococcus lactis* kivD gene,
a region (underlined case) harbouring the EcoRI restriction site The pPAL7-kivDll plasmid was then introduced into the strain BL21 (DE3) competent cells (Invitrogen).

2.2 Overproduction of the Protein Kivd

The overproduction of the protein KivD was done in a 2 l Erlenmeyer flask, using LB broth (Bertani, 1951, J. Bacteriol. 62:293-300) that was supplemented with 2,5 g/l glucose and 100 mg/l of ampicillin. A preculture was grown overnight in a 500 ml Erlenmeyer flask filled with 50 ml of LB broth that was supplemented with 2,5 g/l glucose and 100 mg/l of ampicillin. The preculture was used to inoculate a 500 ml culture to an $OD_{600\,nm}$ of about 0,15. The culture was first grown at 37° C. and 200 rpm until the $OD_{600\,nm}$ was about 0,5 and then shifted to 25° C. and 200 rpm and grown until the $OD_{600\,nm}$ was 0,6-0,8 (about one hour), before induction with 500 μM IPTG. The culture was kept at 25° C. and 200 rpm until $OD_{600nm}$ was around 4, and then stopped. Cells were centrifuged at 7000 rpm for 5 minutes at 4° C., and then stored at −20° C.

2.3 Purification of the Protein KivD 2.3.1—Step 1: Preparation of Cell-Free Extracts.

About 188 mg of *E. coli* biomass was suspended in 30 ml of 100 mM potassium phosphate pH 7.6, and a protease inhibitor cocktail. The cell suspension (15 ml per conical tube) was sonicated on ice (Bandelin sonoplus, 70 W) in a 50 ml conical tube during 8 cycles of 30 sec with 30 sec intervals. After sonication, cells were incubated for 30 min at room temperature with 5 mM MgCl2 and IUI/ml of DNaseI. Cells debris was removed by centrifugation at 12000 g for 30 min at 4° C.

2.3.2—Step 2: Affinity Purification

The protein was purified from crude cell-extract by affinity on a Profinity column (BIORAD, Bio-Scale Mini Profinity exact cartridge 5 ml) according to the protocol recommended by the manufacturer. Crude extract was loaded on a 5 ml Profinity exact cartridge equilibrated with 100 mM potassium phosphate pH 7.6. The column was washed with 10 column volumes of the same buffer and incubated overnight with 100 mM potassium phosphate pH 7.6, 100 mM fluoride at 4° C. The protein was eluted from the column with 2 column volumes of 100 mM potassium phosphate pH 7.6. The tag remained tightly bound to the resin and the purified protein was released. The fractions containing the protein were pooled and dialyzed against 100 mM potassium phosphate, 150 mM NaCl and 10% glycerol pH 8.

Protein concentration was measured using the Bradford protein assay.

2.4 Hydroxy Keto-Acid Decarboxylase Assay 2.4.1—Chemical synthesis of 5-hydroxy-2-ketopentanoic acid Chemical synthesis of 5-hydroxy-2-ketopentanoic acid has been described in the publication:

Friedhelm Korte, Karl Heinz Büchel, α-Hydroxyalkyliden-lacton-Umlagerung, X. α-Hydroxyalkyliden-lacton-Umlagerung in wäBriger Salzsäure Chemische Berichte, Volume 92 Issue 4, Pages 877-883 (1959).

2.4.2—Chemical synthesis of 4-hydroxy-2-ketobutyric acid

Chemical synthesis of 4-hydroxy-2-ketobutyric acid has been described in the publication: R S Lane; E E Dekker; (1969).2-keto-4-hydroxybutyrate. Synthesis, chemical properties, and as a substrate for lactate dehydrogenase of rabbit muscle Biochemistry 8 (7), 2958-2966.

2.4.3—Hydroxy Keto-Acid Decarboxylase Assay

The decarboxylation of hydroxy keto-acids was measured at 30° C. using a coupled enzymatic assay. The hydroxy keto-acid decarboxylase activity assay was carried out with 50 mM potassium phosphate buffer pH 6, 0.2 mM NADH, 1 mM $MgSO_4$, 0.5 mM thiamin diphosphate, 72 units/ml alcohol dehydrogenase from *Saccharomyces cerevisiae*, 10 mM hydroxy keto-acid neutralized (Hydroxypyruvic acid or 4-hydroxy-2-ketobutyric acid or 5-hydroxy-2-ketopentanoic acid) and about 40 μg of purified protein in a total volume of 1 ml. The consumption of NADH was monitored at 340 nm on a spectrophotometer. The activity detected in control assay, lacking the substrate, was subtracted from the activity detected in the assay with substrate. A unit of hydroxy keto-acid decarboxylase activity is the amount of enzyme required to catalyze the decarboxylation of 1 μmol of hydroxy keto-acid per min at 30° C. (Epsilon 340 nm=6290 M−1 cm−1).

2.5 Activity of Purified Enzyme

| | Activity of purified enzyme (mUl/mg) |
|---|---|
| Hydroxypyruvate decarboxylase assay | 79 |
| 4-hydroxy-2-ketobutyrate decarboxylase assay | 147 |
| 5-hydroxy-2-ketopentanoate decarboxylase assay | 63 |

EXAMPLE 3

Demonstration of the hydroxy aldehyde dehydrogenase activity encoded by the gene gabD of *Escherichia coli*

3.1 Construction of the Strain for gabD Characterization: BL21 (pPAL7Vb01-gabD)

To characterise the GabD protein, the corresponding gene was expressed from the expression vector pPAL7 (Bio-rad).

For this purpose, the gabD gene was amplified from the *E. coli* MG1655 genome using the oligonucleotides gabD_pPAL7VB01 F and gabD_pPAL7_pFN18A R. The PCR product was restricted using enzymes HindIII and EcoRI and cloned into the vector pPAL7 restricted by the same restriction enzymes. The resulting vector was named pPAL7VB01-gadD.

```
gabD_pPAL7VB01 F (SEQ ID NO 3):
CCCAAGCTTTGACTTCTATGAAACTTAACGACAGTAAC
``` with
- a region (italic case) homologous to the sequence (2789295-2789315) of the MG1655 gabD gene (reference sequence on the website www.ecogene.org/),
- a region (bold case) harbouring the nucleotides necessary to generate tag-free protein containing a short N-terminal amino acid extension to favour the purification
- a region (underlined case) harbouring the HindIII restriction site

```
gabD_pPAL7_pFN18A R (SEQ ID NO 4):
GTGGGTTTAAACGGAATTCTTAAAGACCGATGCACATATATTTG
``` with
- a region (italic case) homologous to the sequence (2790743-2790719) of the MG1655 gabD gene (reference sequence on the website www.ecogene.org/),
- a region (underlined case) harbouring the EcoRI restriction site The pPAL7VB01-gabD plasmid was then introduced into the strain BL21 (DE3) competent cells (Invitrogen).

3.2 Overproduction of the Aldehyde Dehydrogenase GabD

The overproduction of the protein gabD was done applying the same protocol as example #2.2.

3.3 Purification of the Protein GabD

3.3.1—Step 1: Preparation of Cell-Free Extracts.

About 60 mg of *E. coli* biomass was resuspended in 9 ml of 100 mM potassium phosphate pH 7.6, and a protease inhibitor cocktail. The cell suspension was sonicated on ice (Bandelin sonoplus, 70 W) in a 50 ml conical tube during 8 cycles of 30 sec with 30 sec intervals. After sonication, cells were incubated for 45 min at room temperature with 5 mM MgCl2 and 1 UI/ml of DNaseI. Cells debris was removed by centrifugation at 12000 g for 30 min at 4° C.

3.3.2—Step 2: Affinity Purification

The protein was purified from the crude cell-extract by affinity on a Profinity column (BIORAD, Bio-Scale Mini Profinity exact cartridge 1 ml) according to the protocol recommended by the manufacturer. The crude extract was loaded on a 1 ml Profinity exact cartridge equilibrated with 100 mM potassium phosphate pH 7.6. The column was washed with 10 column volumes of the same buffer and incubated overnight with 100 mM potassium phosphate pH 7.6, 100 mM fluoride at 4° C. The protein was eluted from the column with 2 column volumes of 100 mM potassium phosphate pH 7.6. The tag remained tightly bound to the resin and the purified protein was released. The fractions containing the protein were pooled and dialyzed against 100 mM potassium phosphate, 150 mM NaCl and 10% glycerol pH 8.

Protein concentration was measured using the Bradford protein assay.

3.4 Glycolaldehyde, 3-hydroxypropionaldehyde and 4-hydroxybutyraldehyde dehydrogenase assay Glycolaldehyde, 3-hydroxypropionaldehyde and 4-hydroxybutyraldehyde dehydrogenase activity was assayed by measuring the initial rate of NADP reduction with a spectrophotometer at a wavelength of 340 nm and at a constant temperature of 30° C. The reaction mixture using glycolaldehyde, 3-hydroxypropionaldehyde or 4-hydroxybutyraldehyde as substrate was carried out in 100 mM potassium phosphate buffer pH 7.5, 0.5 mM NADP, about 20 µg of purified enzyme in a final volume of 1 ml. The reaction mixture was incubated for 5 min at 30° C. and then the reaction was initiated by the addition of the substrate (glycoladehyde, 3-hydroxypropionaldehyde or 4-hydroxybutyraldehyde) at a final concentration of 10 mM. Control assay (blank), lacking the substrate was run in parallel and the value measured for the control was subtracted to the value measured for the assay to take into account non-specific reduction of NADP. (Epsilon 340 nm=6290 M−1 cm−1).

One unit of enzyme activity was defined as the amount of enzyme that consumed 1 µmol substrate per minute under the conditions of the assay. Specific enzyme activity was expressed as units per mg of protein.

3.5 Activity of Purified Enzyme

| | Activity of purified enzyme (mUI/mg) |
|---|---|
| Glycolaldehyde dehydrogenase assay | 205 |
| 3-hydroxypropionaldehyde dehydrogenase assay | 258 |
| 4-hydroxybutyraldehyde dehydrogenase assay | 2793 |

EXAMPLE 4

Demonstration of the L-Serine Transaminase and L-Homoserine Transaminase Activity Encoded by the Gene serC of *Escherichia Coli*

4.1 Construction of Strain for serC Characterisation: BL21 (pPAL7-serC)

To characterise the SerC protein, the corresponding gene was expressed from the expression vector pPAL7 (Bio-rad). For this purpose, the serC gene was amplified from the *E. coli* genome using the oligonucleotides pPAL7-serC F and pPAL7-serC R. The PCR product was restricted using enzymes HindIII and EcoRI and cloned into the vector pPAL7 restricted by the same restriction enzymes. The resulting vector was named pPAL7-serC.

```
pPAL7-serC F (SEQ ID NO 5):
cccAAGCTTtgATGGCTCAAATCTTCAATTTTAGTTCTGG
``` with
- a region (bold case) homologous to the sequence (956876-956904) of the gene serC (reference sequence on the website www.ecogene.org/),
- a region (underlined case) harbouring the HindIII restriction site

```
pPAL7-serC R (SEQ ID NO 6):
gGAATTCTTAACCGTGACGGCGTTCGAACTCAACC
``` with
- a region (bold case) homologous to the sequence (957964-957937) of the gene serC region (reference sequence on the website www.ecogene.org/),
- a region (underlined case) harbouring the EcoRI restriction site.

The pPAL7-serC plasmid was then introduced into competent BL21 (DE3) cells (Invitrogen).

4.2 Overproduction of the Protein SerC

The overproduction of the protein SerC was done applying the same protocol as example #2.2

4.3 Purification of the protein SerC

4.3.1—Step 1: Preparation of Cell-Free Extracts.

About 280 mg of *E. coli* biomass was suspended in 45 ml of 100 mM potassium phosphate pH 7.6, and a protease inhibitor cocktail. The cell suspension (15 ml per conical tube) was sonicated on ice (Bandelin sonoplus, 70 W) in a 50 ml conical tube during 8 cycles of 30 sec with 30 sec intervals. After sonication, cells were incubated for 30 min at room temperature with 5 mM MgCl2 and IUI/ml of DNaseI. Cells debris was removed by centrifugation at 12000 g for 30 min at 4° C.

4.3.2—Step 2: Affinity Purification

The protein was purified from the crude cell-extract by affinity on a Profinity column (BIORAD, Bio-Scale Mini Profinity exact cartridge 5 ml) according to the protocol recommended by the manufacturer. The crude extract was loaded on a 5 ml Profinity exact cartridge equilibrated with 100 mM potassium phosphate pH 7.6. The column was washed with 10 column volumes of the same buffer and incubated 30 min with 100 mM potassium phosphate pH 7.6, 100 mM fluoride at room temperature. The protein was eluted from the column with 2 column volumes of 100 mM potassium phosphate pH 7.6. The tag remained tightly bound to the resin and the purified protein was released. The fractions containing the protein were pooled and dialyzed against 100 mM Tris HCl, 150 mM NaCl and 10% glycerol pH 8.

Protein concentration was measured using the Bradford protein assay.

4.4 L-serine Transaminase Activity Assay

For the L-serine transaminase activity assay about 30 ng of purified enzyme was added to a buffer containing 50 mM Tris-HCl buffer pH 8.2, 3 mM L-Serine, 1 mM α-ketoglutaric acid in a total volume of 300 µl. The reaction was incubated during 60 min at 30° C. The reaction product (hydroxypyruvic acid) was measured directly by LC-MS/MS.

4.5 L-Homoserine Transaminase Assay

The L-homoserine transaminase activity was measured at 30° C. using a coupled enzymatic assay. The L-homoserine transaminase activity assay was carried out with 420 mM potassium phosphate buffer pH 8.2, 2 mM acetylpyridine adenine dinucleotide, 3 mM L-homoserine, 20 units/ml glutamic dehydrogenase from bovine liver, 1 mM alpha-ketoglutaric acid neutralized and about 50 µg of crude extract in a total volume of 1 ml. The consumption of acetylpyridine adenine dinucleotide was monitored at 375 nm on a spectrophotometer. The activity detected in control assay, lacking the substrate (L-homoserine), was subtracted from the activity detected in the assay with substrate. A unit of L-homoserine transaminase activity is the amount of enzyme required to catalyze the transamination of 1 mmol of L-homoserine per min at 30° C. (Epsilon 375 nm=6100 M−1 cm−1).

4.6 Activities of Purified Enzyme

|  | Activity of purified enzyme (mUI/mg) |
|---|---|
| L-Serine transaminase assay | 186 |
| L-Homoserine transaminase assay | 118 |

EXAMPLE 5

Demonstration of the 3-Phosphohydroxypyruvate Phosphatase Activity Encoded by the gene GPP2 of *Saccharomyces cerevisiae*

5.1 Construction of a Strain for GPP2Sc Characterization: BL21 (pPAL7-GPP2Sc)

To characterise the GPP protein, the corresponding gene was expressed from the expression vector pPAL7 (Bio-rad).

For this purpose, the gpp gene was amplified from the *Saccharomyces cerevisiae* genome using the oligonucleotides pPAL7-gpp2sc F and pPAL7-gpp2sc R. The PCR product was restricted using enzymes HindIII and BamHI and cloned into the vector pPAL7 restricted by the same restriction enzymes. The resulting vector was named pPAL7-gpp2sc.

```
pPAL7-gpp2sc F (SEQ ID NO 7):
    cccAAGCTTTgATGGGATTGACTACTAAACCTCTATC
``` with
- a region (bold case) homologous to the sequence (280680-280655) of the gene gpp2 region (reference sequence on the website www.yeastgenome.org/),
- a region (underlined case) harbouring the HindIII restriction site

```
pPAL7-gpp2sc R (SEQ ID NO 8):
    gGGATCCTTACCATTTCAACAGATCGTCCTTAGC
``` with
- a region (bold case) homologous to the sequence (279928-279954) of the gene gpp2 region (reference sequence on the website www.yeastgenome.org/),
- a region (underlined case) harbouring the BamHI restriction site.

The pPAL7-gpp2sc plasmid was then introduced into competent BL21 (DE3) cells (Invitrogen).

5.2 Overproduction of the Protein GPP2Sc

The overproduction of the protein GPP2sc was done applying the same protocol as example #2.2

5.3 Purification of the protein GPP2sc

5.3.1—Step 1: Preparation of Cell-Free Extracts

About 294 mg of *E. coli* biomass was suspended in 45 ml of 100 mM potassium phosphate pH 7.6, and a protease inhibitor cocktail. The cell suspension (15 ml per conical tube) was sonicated on ice (Bandelin sonoplus, 70 W) in a 50 ml conical tube during 8 cycles of 30 sec with 30 sec intervals. After sonication, cells were incubated for 30 min at room temperature with 5 mM MgCl2 and 1 UI/ml of DNaseI. Cells debris was removed by centrifugation at 12000 g for 30 min at 4° C.

5.3.2—Step 2: Affinity purification

The protein was purified from the crude cell-extract by affinity on a Profinity column (BIORAD, Bio-Scale Mini Profinity exact cartridge 5 ml) according to the protocol recommended by the manufacturer. The crude extract was loaded on a 5 ml Profinity exact cartridge equilibrated with 100 mM potassium phosphate pH 7.6. The column was washed with 10 column volumes of the same buffer and incubated overnight with 100 mM potassium phosphate pH 7.6, 100 mM fluoride at room temperature. The protein was eluted from the column with 2 column volumes of 100 mM potassium phosphate pH 7.6.

The tag remained tightly bound to the resin and the purified protein was released. The fractions containing the protein were pooled and dialyzed against 100 mM potassium phosphate, 150 mM NaCl, 10% glycerol pH 8 and concentrated to a concentration of 0.22 µg/µl.

Protein concentration was measured using the Bradford protein assay.

5.4 3-phosphohydroxypyruvate Phosphatase Activity Assay

5.4.1—Chemical synthesis of 3-phosphohydroxypyruvate

Chemical synthesis of 3-phosphohydroxypyruvate has been described in the publication: C E Ballou; H Hesse; R Hesse; (1956). The Synthesis and Properties of Hydroxypyruvic Acid Phosphate J Am Chem. Soc., 78 (15), 3718-3720.

5.4.2—3-Phosphohydroxypyruvate Phosphatase Activity Assay 3-phosphohydroxypyruvate phosphatase activity assay was carried out with 50 mM Tris-HCl buffer pH 8.2, 5 mM $MgCl_2$, 3.6 mM 3-phosphohydroxypyruvate and about 6 µg of purified enzyme (Gpp) in a total volume of 300 µl. The reaction was incubated during 120 min at 30° C. The reaction product (hydroxypyruvic acid) was measured directly by LC-MS/MS.

5.5 Activity of Purified Enzyme

|  | Activity of purified enzyme (mUI/mg) |
|---|---|
| 3-phosphohydroxypyruvate phosphatase assay | 9 |

EXAMPLE 6

Construction of a strain expressing a 2-keto acid decarboxylase and aldehyde dehydrogenase encoding genes: MG1655 (pBBR1MCS5-Ptrc01/RBS01*2-aldH-kivDll-TT07) and MG1655 (pBBR1MCS5-Ptrc01/RBS01*2-gabD-kivDll-TT07) and MG1655 (pBBR1MCS5-Ptrc01/RBS01*2-ald-4-kivDll-TT07).

6.1 Construction of a Plasmid for the Overexpression of the Methylglyoxal Reductase yqhD gene of *Escherichia coli* and the Alpha-Ketoisovalerate Decarboxylase kivD Gene of *Lactococcus lactis*: pBBR1MCS5-Ptrc01/RBS01*2-yqhD-kivDll-TT07 plasmid The pME101-yqhD-kivDll-TT07 plasmid was first constructed. The kivDll gene from the pME101-kivDll-TT07 vector (previously described in PCT/2009/067994) was restricted by BsrBI and BglII and cloned into the pME101VB01-yqhD vector (previously described in PCT/2007/000509) restricted by the same enzymes, the resulting plasmid was named pME101-yqhD-kivDll-T07.

The yqhD and kivDll genes were then PCR amplified from the pME101-yqhD-kivDll-TT07 plasmid with the oligonucleotides Ptrc01-RBS01-yqhD pBBR F and kivD pBBR R. The PCR product was digested with the restriction enzymes SpeI and SmaI and cloned into the vector pBBR1MCS5 (M. E. Kovach, (1995), Gene 166:175-176) restricted by the same enzymes giving the pBBR1MCS5-Ptrc01/RBS01*2-yqhD-kivDll-TT07 vector.

Ptrc01-RBS01-yqhD pBBR F (SEQ ID NO 9)

AgaACTAGTgagctgttgacaattaatcatccggctcgtataatgtgtggaagtcgacGGATCCtaaggaggttat aaatgaacaactttaatctgcacacccc with
- a region (bold upper case) harbouring a SpeI restriction site
- a region (bold lower case) harbouring the constitutive Ptrc promoter sequence
- a region (italic upper case) harbouring a BamHI restriction site
- a region (underlined lower case) harbouring the Ribosome Binding Site sequence
- a region (italic lower case) homologous to the sequence (3153377-3153402) of the MG1655 yqhD gene (reference sequence on the website www.ecogene.org/)

kivD pBBR R (SEQ ID NO 10)

GAG*CCCGGG*GCAGAAAGGCCCACCCGAAGGTGAGCCAGTGTGATACGT

AGAATTCTTAATTAAGT*TAGCTTTTATTCTGTTCGGCG* with
- a region (bold italic upper case) harbouring a SmaI restriction site
- a region (underlined upper case) harbouring the T7Te transcriptional terminator sequence from T7 phage (Harrington K.J., Laughlin R.B. and Liang S. Proc Natl Acad Sci USA. 2001 Apr. 24; 98(9):5019-24.),
- a region (bold upper case) harbouring a SnaBI, EcoRI, PacI restriction sites
- a region (italic upper case) homologous to the end of the synthetic kivD gene 6.2 Construction of a Plasmid for the Overexpression of the Aldehyde Dehydrogenase aldH Gene of *Escherichia coli* and the Alpha-Ketoisovalerate Decarboxylase Kivd Gene of *Lactococcus lactis*: pBBR1MCS5-Ptrc01/RBS01*2-aldH-kivDll-TT07 Plasmid For the pBBR1MCS5-Ptrc01/RBS01*2-aldH-kivDll-TT07 vector construction, the aldH gene was amplified from the *E. coli* MG1655 genome using the oligonucleotides RBS01*2-aldH pBBR F and aldH pBBR R. The PCR product was restricted using enzymes BamHI and NheI and cloned into the vector pME101-yqhD-kivDll-TT07 restricted by the same enzymes. The resulting vector was named pBBR1MCS5-Ptrc01/RBS01*2-aldH-kivDll-TT07.

RBS01*2-aldH pBBR F (SEQ ID NO 11):
ACGC<u>GTCGACGGATCC</u>*TAAGGAGGTTATAA*ATGAATTTTCATCATCTGG

CTTACTGGCAGG with
- a region (underlined bold upper case) harbouring a SalI—BamHI restriction sites
- a region (italic upper case) harbouring the Ribosome Binding Site sequence
- a region (bold upper case) homologous to the sequence (1360767-1360797) of the MG1655 aldH gene (reference sequence on the website www.ecogene.org/), aldH pBBR R (SEQ ID NO 12):
CTA<u>GCTAGCGAATTCTTAATTAAG</u>TCAGGCCTCCAGGCTTATCCAGATG

GTTTTC with
- a region (underlined case) harbouring a NheI-EcoRI-PacI restriction sites
- a region (italic case) homologous to the sequence (1362254-1362224) of the MG1655 aldH gene (reference sequence on the website www.ecogene.org/), The pBBR1MCS5-Ptrc01/RBS01*2-a/dH-kivDll-TT07 plasmid was then introduced into the strain MG1655.

6.3 Construction of a plasmid for the overexpression of the aldehyde dehydrogenase gabD gene of *Escherichia coli* and the alpha-ketoisovalerate decarboxylase kivD gene of *Lactococcus lactis*: pBBR1MCS5-Ptrc01/RBS01*2-gabD-kivDll-TT07 plasmid For the pBBR1MCS5-Ptrc01/RBS01*2-gabD-kivDll-TT07 vector construction, the gabD gene was amplified from the *E. coli* MG1655 genome using the oligonucleotides RBS01*2-gabD pBBR F and gabD pBBR R. The PCR product was restricted using enzymes BamHI and NheI and cloned into the vector pME101-yqhD-kivDll-TT07 restricted by the same restriction enzymes. The resulting vector was named pBBR1MCS5-Ptrc01/RBS01*2-gabD-kivDll-TT07.

RBS01*2-gabD pBBR F (SEQ ID NO 13):
ACGC<u>GTCGACGGATCC</u>*TAAGGAGGTTATAA*ATGAAACTTAACGACAGTA

ACTTATTCCGCC with
- a region (underlined bold upper case) for addition of a SalI—BamHI restriction sites
- a region (italic upper case) for addition of the Ribosome Binding Site sequence
- a region (bold upper case) homologous to the sequence (2789295-2789325) of the MG1655 gabD gene (reference sequence on the website www.ecogene.org/),

```
gabD pBBR R (SEQ ID NO 14):
CTAGCTAGCGAATTCTTAATTAAGTTAAAGACCGATGCACATATATTTG
ATTTC
``` with
- a region (underlined case) for addition of a NheI-EcoRI-PacI restriction sites
- a region (italic case) homologous to the sequence (2790745-2790714) of the MG1655 gabD gene (www.ecogene.org/), The pBBR1MCS5-Ptrc01/RBS01*2-gabD-kivDll-TT07 plasmid was then introduced into the strain MG1655.

6.4 Construction of a Plasmid for the Overexpression of the Aldehyde Dehydrogenase ald4 Gene of *Saccharomyces cerevisiae* and the Alpha-Ketoisovalerate Decarboxylase kivD gene of *Lactococcus lactis*: pBBR1MCS5-Ptrc01/RBS01*2-ald-4-kivDll-TT07 plasmid For the pBBR1MCS5-Ptrc01/RBS01*2-ald-4-kivDll-TT07 vector construction, the ald4 gene was amplified from the *S. cerevisiae* BY4743 genome using the oligonucleotides RBS01*2-ald4 sc pBBR F and ald4 sc pBBR R. The PCR product was restricted using enzymes BamHI and NheI and cloned into the vector pME101-yqhD-kivDll-TT07 restricted by the same restriction enzymes. The resulting vector was named pBBR1MCS5-Ptrc01/RBS01*2-ald-4-kivDll-TT07.

```
RBS01*2-ald4 sc pBBR F (SEQ ID NO 15):
ACGCGTCGACGGATCCTAAGGAGGTTATAAATGTTCAGTAGATCTACGC
TCTGC
``` with
- a region (underlined bold upper case) for addition of a SalI—BamHI restriction sites
- a region (italic upper case) for addition of the Ribosome Binding Site sequence
- a region (bold upper case) homologous to the sequence (1039838-1039861) of the *S. cerevisiae* ald4 gene (reference sequence on the website www.yeastgenome.org/),

```
ald4 sc pBBR R (SEQ ID NO 16):
CTAGCTAGCGAATTCTTAATTAAGTTACTCGTCCAATTTGGCACGGACC
GC
``` with
- a region (underlined case) for addition of a NheI-EcoRI—PacI restriction sites
- a region (italic case) homologous to the sequence (1041371)1041397 of the *S. cerevisiae* ald4 gene (www.yeastgenome.org/), The pBBR1MCS5-Ptrc01/RBS01*2-ald-4-kivDll-TT07 plasmid was then introduced into the strain MG1655.

6.5 Overproduction of the 2-Keto Acid Decarboxylase kivDll and the Three Aldehyde dehydrogenases AldH, GabD and Ald4

The overproduction of proteins KivDll and AldH or GabD or Ald4 was done in 500 ml baffled Erlenmeyer flask cultures using modified M9 medium (Anderson, 1946, Proc. Natl. Acad. Sci. USA 32:120-128) that was supplemented with 10 g/l MOPS and 10 g/l glucose and adjusted at pH 6,8. Gentamicin was added at a concentration of 50 mg/l. An overnight preculture was used to inoculate a 50 ml culture to an $OD_{600nm}$ of about 0,4. The culture was kept on a shaker at 37° C. and 200 rpm until $OD_{600nm}$ was around 4, and then it was stopped. Cells are centrifuged at 7000 rpm, 5 minutes at 4° C., and then stored at −20° C.

6.6 Crude Extracts Preparation

About 25 mg dry weight of *E. coli* biomass was resuspended in 1 mL of 100 mM potassium phosphate pH 7.6 containing 0.1 mM DTT, 0.1 mM pyridoxal 5'-phosphate (PLP) and a protease inhibitor cocktail. The cell suspension was transferred to a microtube containing 0.1 mm glass beads and proteins were extracted by placing the microtube in a Precellys 24 (Bertin Technologies) during 30 seconds. After lysis, cells debris was removed by centrifugation at 12000 g for 30 min at 4° C. Crude extracts were desalted using a 5 mL Zeba desalt spin column (Thermo).

6.7 Glycolaldehyde, 3-hydroxypropionaldehyde and 4-hydroxybutyraldehyde dehydrogenase assay Glycolaldehyde, 3-hydroxypropionaldehyde and 4-hydroxybutyraldehyde dehydrogenase activity was assayed by measuring the initial rate of NAD (for AldH and Ald4) or NADP (for GabD) reduction with a spectrophotometer at a wavelength of 340 nm and at a constant temperature of 30° C. The reaction mixture using glycolaldehyde, 3-hydroxypropionaldehyde or 4-hydroxybutyraldehyde as substrate was carried out in 100 mM potassium phosphate buffer pH 7.5, 0.5 mM NAD or NADP, and about 5 pg of crude extract in a final volume of 1 mL. The reaction mixture was incubated for 5 min at 30° C. then the reaction was initiated by the addition of the substrate (glycoladehyde, 3-hydroxypropionaldehyde or 4-hydroxybutyraldehyde) at a final concentration of 10 mM. A control assay (blank) lacking the substrate was run in parallel and the value measured for the control was subtracted from the value measured for the assay so as to take into account non-specific reduction of NAD or NADP. (Epsilon for NADH or NADPH at 340 nm=6290 M−1 cm−1).

One unit of enzyme activity was defined as the amount of enzyme that consumed 1 μmol substrate per minute under the conditions of the assay. Specific enzyme activity was expressed as units per mg of protein.

6.8 Activity of Crude Extracts Expressing Different Aldehydes Dehydrogenases

| Genotype | Glycol-aldehyde dehydrogenase assay | 3-Hydroxypropionaldehyde dehydrogenase assay | 4-Hydroxybutyraldehyde dehydrogenase assay |
|---|---|---|---|
| MG1655 | 0 | 0 | 0 |
| MG1655 (pBBR1MCS5-Ptrc01/RBS01*2-gabD-kivDII-TT07) | 75 | 125 | 1 761 |
| MG1655 (pBBR1MCS5-Ptrc01/RBS01*2-aldH-kivDII-TT07) | 1860 | 3 384 | 2 637 |
| MG1655 (pBBR1MCS5-Ptrc01/RBS01*2-ald4-kivDII-TT07) | ND | ND | ND |

ND: Not Determined

Demonstration of enzyme activities hydroxy keto-acid decarboxylase (#2.5) combined to glycolaldehyde dehydrogenase or 3-hydroxypropionaldehyde dehydrogenase or 4-hydroxybutyraldehyde dehydrogenase confirms that the described pathways can be used for the production of hydroxyacetate or 3-hydroxypropionate or 4-hydroxybutyrate respectively.

EXAMPLE 7

Construction Of a Strain With Increased Hydroxyacetate Pathway Flux Expressing a 2-Keto Acid Decarboxylase, a Hydroxy Aldehyde Reductase, a Phosphohydroxy Pyruvate Phosphatase and a Phosphoglycerate Dehydrogenase Encoding Genes: Mg1655 ΔpykF (pME101-Ptrc01/RBS01*2-aldH-kivDll-yeaB-TT07) (pCC1BAC-serA)

7.1 Construction of the strain MG1655 ΔpykF

To delete the pykF gene, the homologous recombination strategy described by Datsenko and Wanner (2000) was used as previously described. For this purpose the following oligonucleotides were used:

```
ΔpykFF
                                        (SEQ ID NO 17)
cccatccttctcaacttaaagactaagactgtcatgaaaaagaccaaaa ttgtttgcaccatcggaccgaaaaccgaaTGTAGGCTGGAGCTGCTTCG
``` with
- a region (lower case) homologous to the sequence (1753689-1753766) of the MG1655 pykF region (reference sequence on the website www.ecogene.org/),
- a region (upper case) for the amplification of the kanamycin resistance cassette,

```
ΔpykFR
                                        (SEQ ID NO 18)
ggacgtgaacagatgcggtgttagtagtgccgctcggtaccagtgcaccagaaaccataactacaacgtcacctttgtgCATA

TGAATATCCTCCTTAG
``` with
- a region (lower case) homologous to the sequence (1755129-1755051) of the MG1655 pykF region (reference sequence on the website www.ecogene.org/),
- a region (upper case) for the amplification of the kanamycin resistance cassette.

The oligonucleotides ΔpykFF and ΔpykFR were used to amplify the kanamycin resistance cassette from the plasmid pKD4. The PCR product obtained was then introduced by electroporation into the strain MG1655 (pKD46). The kanamycin resistant transformants were then selected and the insertion of the resistance cassette was verified by a PCR analysis with the oligonucleotides pykFF and pykFR defined below. The strain retained was designated MG1655 ΔpykF::Km.

```
pykFF (SEQ ID NO 19):
gcgtaaccttttccctggaacg
(homologous to the sequence
from 1753371 to 1753392).

pykFR (SEQ ID NO 20):
gcgttgctggagcaacctgccagc
(homologous to the sequence
from 1755518 to 1755495).
```

The kanamycin resistance cassette was eliminated. The plasmid pCP20 carrying FLP recombinase acting at the FRT sites of the kanamycin resistance cassette was then introduced into the recombinant strain by electroporation. After a series of cultures at 42° C., the loss of the kanamycin resistance cassettes was verified by a PCR analysis with the same oligonucleotides as used previously (pykFF/pykFR). The strain retained was designated MG1655 ΔpykF.

7.2 Construction of a Plasmid for Overexpression of the Phosphoglycerate Dehydrogenase serA of *Escherichia coli*: pCC1BAC-serA Plasmid To increase the expression of the serA gene, the gene is expressed from the copy control vector pCC1BAC (Epicentre) using its proper promoter.

For this purpose, the serA gene is amplified from the *E. coli* genome using the oligonucleotides serA F and serA R. The PCR product is restricted using enzymes XbaI and SmaI and cloned into the vector pUC18 (Stratagene) restricted by the same enzymes.

The resulting vector is named pUC18-serA.

```
serA F (SEQ ID NO 21):
ctagTCTAGATTAGTACAGCAGACGGGCGCG
``` with
- a region (upper case) homologous to the sequence (3055199-3055220) of the MG1655 serA gene (reference sequence on the website www.ecogene.org/),
- a region (bold upper case) harbouring the XbaI site

```
serA R (SEQ ID NO 22):
tccCCCGGGAAGCTTCCGTCAGGGCGTGGTGACCG
``` with
- a region (upper case) homologous to the sequence (3056880-3056861) of the MG1655 serA gene region (reference sequence on the website www.ecogene.org/),
- a region (bold upper case) harbouring the SmaI and HindIII sites.

To transfer the gene serA into the copy control vector pCC1BAC, the vector pUC18-serA is restricted with the enzyme Hindu and cloned into HindIII cloning ready pCC1BAC (Epicentre). The resulting construct is verified and named pCC1BAC-serA.

7.3 Construction of a Plasmid for Overexpression of the Alpha-Ketoisovalerate Decarboxylase Kivd Gene of *Lactococcus lactis*, the Aldehyde Dehydrogenase aldH and the 3-Phospho hydroxypyruvate yeaB Genes of *Escherichia coli*: pBBR1MCS5-Ptrc01/RBS01*2-aldH-kivDll-yeaB-TT07 Plasmid The yeaB gene is PCR amplified from genomic DNA of the *E. coli* MG1655 strain with the oligonucleotides pBBR yeaB F and pBBR yeaB R. The PCR product is digested with the restriction enzymes SnaBI and SmaI and cloned into the vector pBBR1MCS5-Ptrc01/RBS01*2-aldH-kivDll-TT07 (previously described) restricted by the same enzymes, giving the pBBR1MCS5-Ptrc01/RBS01*2-aldH-kivDll-yeaB-TT07 vector.

```
pBBR yeaB F
                                        (SEQ ID NO 23)
AGCTTACGTAtaaggaggtatattATGGAATACCGTAGCCTGACGC
``` a region (italic bold upper case) harbouring a SnaBI restriction sites a region (underlined lower case) harbouring a Ribosome Binding Site sequence a region (upper case) homologous to the *E. coli* MG1655 yeaB region from 1894195 to 1894215 (www.ecogene.org/), ΔmetAF (SEQ ID NO 25):
ttcgtgtgccggacgagctacccgccgtcaatttcttgcgtgaagaaaacgtctttgtgatgacaacttctcgtgcgtctTGTAG

GCTGGAGCTGCTTCG pBBR yeaB R
(SEQ ID NO 24)
GC*cccggg*TAG<u>CAGAAAGGCCCACCCGAAGGTGAGCCAGGA</u>GTATACAT -continued
*GAAGCATTTCCGTTAATTAACGGAGCTCATCCTAGG*TCAGGGTTTCACA

CCAATTTGCAGCGCC a region (bold upper case) homologous to the *E. coli* MG1655 yeaB region from 1894772 to 1894745 (www.ecogene.org/), a region (underlined upper case) for amplification of the terminator sequence T7Te (ref: Harrington K. J., Laughlin R. B. and Liang S. Proc Natl Acad Sci USA. 2001 Apr. 24; 98(9):5019-24.):

a region (italic lower case) harbouring a SmaI restriction site

The pBBR1MCS5-Ptrc01/RBS01*2-aldH-kivDll-yeaB-TT07 plasmid is then introduced into the strain MG1655.

7.4 Construction of the Strain MG1655 ΔpykF (pME101-Ptrc01/RBS01*2-aldH-kivdll -yeaB-TT07) (pCC1BAC-serA)

The pCC1BAC-serA and pME101-Ptrc01/RBS01*2-aldH-kivDll-yeaB-TT07 plasmids are then introduced into the strain MG1655 ΔpykF.

7.5 Culture for Hydroxyacetate Production

Performances of strains are assessed in 500 ml baffled Erlenmeyer flask cultures using modified M9 medium (Anderson, 1946, Proc. Natl. Acad. Sci. USA 32:120-128) that is supplemented with 10 g/l MOPS and 10 g/l glucose and adjusted at pH 6,8. Spectinomycin, kanamycin and/or gentamicin are added if necessary at a concentration of 50 mg/l, and/or chloramphenicol is added if necessary at a concentration of 60 mg/l. A 24 hours preculture is used to inoculate a 50 ml culture to an $OD_{600nm}$ of about 0.1 to 0.3. The cultures are kept on a shaker at 37° C. and 200 rpm until the glucose in the culture medium is exhausted. At the end of the culture, glucose and major products are analyzed by HPLC using a Biorad HPX 97H column for the separation and a refractometer for the detection. Production of hydroxyacetate is confirmed by LC/MS/MS.

EXAMPLE 8

Construction of strain with increased 3-hydroxypropionate pathway flux expressing a 2-keto acid decarboxylase, a hydroxy aldehyde reductase and a L-homoserine transaminase encoding genes: MG1655 ΔpykF ΔmetA ΔthrLABC (pBBR1MCS5-Ptrc01/RBS01*2-aldH-kivDll-TT07) (pME101-thrA*1-serC)

8.1 Construction of the strain MG1655 ΔpykF ΔmetA

To delete the metA gene, the homologous recombination strategy described by Datsenko & Wanner (2000) was used as previously described. For this purpose the following oligonucleotides were used.

with
a region (lower case) homologous to the sequence (4212310-4212389) of the MG1655 metA region (reference sequence on the website www.ecogene.org/),
a region (upper case) for the amplification of the kanamycin resistance cassette ΔmetAR (SEQ ID NO 26):
atccagcgttggattcatgtgccgtagatcgtatggcgtgatctggtagacgtaatagttgagccagttggtaaacagtaCATAT

GAATATCCTCCTTAG with
a region (upper case) homologous to the sequence (4213229-4213150) of the MG1655 metA region (reference sequence on the website www.ecogene.org/),
a region (upper case) for the amplification of the kanamycin resistance cassette.

The oligonucleotides ΔmetAF and ΔmetAR were used to amplify the kanamycin resistance cassette from the plasmid pKD4. The PCR product obtained was then introduced by electroporation into the strain MG1655 (pKD46). The kanamycin resistant transformants were then selected and the insertion of the resistance cassette was verified by a PCR analysis with the oligonucleotides metAF and metAR defined below. The strain retained was designated MG1655 ΔmetA::Km.

metAF (SEQ ID NO 27):
tcaccttcaacatgcaggctcgacattggc
(homologous to the sequence from 4212203 to 4212232).

metAR (SEQ ID NO 28):
ataaaaaaggcacccgaaggtgcctgaggt
(homologous to the sequence from 4213301 to 4213272).

To transfer the ΔmetA::Km, the method of phage P1 transduction (previously described in PCT/2009/067994) was used. The preparation of the phage lysate from the strain MG1655 ΔmetA::Km was used for the transduction into the strain MG1655 ΔpykF.

The kanamycin resistant transformants were then selected and the ΔmetA::Km was verified by a PCR analysis with the previously defined oligonucleotides metF/metAR. The strain retained was designated MG1655 ΔpykF ΔmetA::Km.

The kanamycin resistance cassette was eliminated. The plasmid pCP20 carrying FLP recombinase acting at the FRT sites of the kanamycin resistance cassette was then introduced into the recombinant strain by electroporation. After a series of cultures at 42° C., the loss of the kanamycin resistance cassette was verified by a PCR analysis with the same oligonucleotides as used previously (pykFF/pykFR, and metF/metAR). The strain retained was designated MG1655 ΔpykF ΔmetA.

8.2 Construction of the Strain MG1655 Δpykf Δmeta ΔthrLABC

To delete the thrLABC operon, the homologous recombination strategy described by Datsenko & Wanner (2000) was used as previously described. For this purpose the following oligonucleotides were used.

```
DthrLABF (SEQ ID NO 29):
cgggcaatatgtctctgtgtggattaaaaaaagagtgtctgatagcagcttctgaactggttaccttctggctcaccttcgggtggg cctttctggtatacTGTAGGCTGGAGCTGCTTCG
``` with
- a region (lower case) homologous to the sequence (22-86) of the MG1655 thrLABC region (reference sequence on the website www.ecogene.org/),
- a region (bold underlined lower case) harbouring the T7Te transcriptional terminator sequence from T7 phage (Harrington K. J., Laughlin R. B. and Liang S. Proc Natl Acad Sci USA. 2001 Apr. 24; 98(9):5019-24.),
- a region (upper case) for the amplification of the chloramphenicol resistance cassette.

```
DthrLABCR (SEQ ID NO 30):
CCCTGTCATTTTTCTCCATAATTTCTTCATAAAAAAGCCGGGCTGCATA

AAAGCAAACCCGGCCTGATTGAGATAATGAATAGATTCCCGGGGGAGGC

GCCCGCGGATCCCATATGAATATCCTCCTTAG
``` with
- a region (upper case) homologous to the sequence (5106-5021) of the MG1655 thrLABC region (reference sequence on the website www.ecogene.org/),
- a region (underlined upper case) harbouring of a BamHI- SfoI- SmaI restriction sites
- a region (bold upper case) for the amplification of the chloramphenicol resistance cassette.

The oligonucleotides DthrLABF and DthrLABCR were used to amplify the chloramphenicol resistance cassette from the plasmid pKD3. The PCR product obtained was then introduced by electroporation into the strain MG1655 (pKD46). The chloramphenicol resistant transformants were then selected and the insertion of the resistance cassette was verified by a PCR analysis with the oligonucleotides thrLF and thrCR defined below. The strain retained was designated MG1655 ΔthrLABC::Cm.

```
thrLF (SEQ ID NO 31):
GCCATGCCGCGCTGGTGTTTGGTCGCG
(homologous to the sequence
from 4639281 to 4639307).

thrCR (SEQ ID NO 32):
GCGACCAGAACCAGGGAAAGTGCG
(homologous to the sequence
from 5283 to 5260).
```

To transfer the ΔthrLABC::Cm, the method of phage P1 transduction was used. The preparation of the phage lysate from the strain MG1655 ΔthrLABC::Cm was used for the transduction into the strain MG1655 ΔpykF ΔmetA. The chloramphenicol resistant transformants were then selected and the ΔthrLABC::Cm was verified by a PCR analysis with the previously defined oligonucleotides thrLF and thrCR. The strain retained was designated MG1655 ΔpykF ΔmetA ΔthrLABC::Cm.

The chloramphenicol resistance cassette was eliminated. The plasmid pCP20 carrying FLP recombinase acting at the FRT sites of the chloramphenicol resistance cassettes was then introduced into the recombinant strain by electroporation. After a series of cultures at 42° C., the loss of the chloramphenicol resistance cassette was verified by a PCR analysis with the same oligonucleotides as used previously (pykFF/pykFR, metAF/metAR, and thrLF/thrCR). The strain retained was designated MG1655 ΔpykF ΔmetA ΔthrLABC.

8.3 Construction of a Plasmid for Overexpression of the L-Homoserine Transaminase serC of *Escherichia coli*: pME101-thrA*1-serC Plasmid To increase the expression of the serC gene, the gene was expressed from the pME101-thrA*1 (previously described in WO2008707041) using its proper promoter.

For this purpose, the serC gene was amplified from the *E. coli* MG1655 genome using the oligonucleotides serC F and serC R. The PCR product was restricted using enzymes XbaI and SmaI and cloned into the vector pME101-thrA*1 restricted by the same enzymes. The resulting vector was named pME101-thrA*1-serC.

```
serC F (SEQ ID NO 33):
TGCTCTAGAGTCCGCGCTGTGCAAATCCAGAATGG
``` with
- a region (upper case) homologous to the sequence (956619-956644) of the MG1655 serC gene (reference sequence on the website www.ecogene.org/),
- a region (bold upper case) harbouring the XbaI site

```
serC R (SEQ ID NO 34):
CCCAAGCTTAACTCTCTACAACAGAAATAAAAAC
``` with
- a region (upper case) homologous to the sequence (958028-958004) of the MG1655 serC gene region (reference sequence on the website www.ecogene.org/),
- a region (bold upper case) harbouring the HindIII site The PCR amplified fragment was digested with the restriction enzymes XbaI and HindIII and cloned into the XbaI—HindIII sites of the vector pME101-thrA*1 giving the pME101-thrA*1-serC.

8.4 Construction of the Strain Mg1655 ΔpykE Δmeta Δthrlabc (Pme101-Thra*1-serC) (pBBR1MCS5-Ptrc01/RBS01*2-aldH-kivD1'-TT07)

The pME101-thrA*1-serC and pBBR1MCS5-Ptrc01/RBS01*2-aldH-kivDll-TT07 plasmids were then introduced into the strain MG1655 ΔmetA ΔpykF ΔthrLABC.

8.5 Construction of the strain MG1655 ΔpykE ΔmetA ΔthrLABC (pME101-thrA*1-serC) (pBBR1MCS 5-Ptrc01/RBS01*2-gabD-kivD1'-TT07)

The pME101-thrA*1-serC and pBBR1MCS5-Ptrc01/RBS01*2-gabD-kivDll-TT07 plasmids were then introduced into the strain MG1655 ΔmetA ΔpykF ΔthrLABC.

8.6 Construction of the strain MG1655 ΔpykE ΔmetA Δthr-LABC (pME101-thrA*1-serC) (pBBR1MCS5-Ptrc01/RBS01*2-ald-4-kivD1'-TT07)

The pME101-thrA*1-serC and pBBR1MCS5-Ptrc01/RBS01*2-ald-4-kivDll-TT07 plasmids were then introduced into the strain MG1655 ΔmetA ΔpykF ΔthrLABC.

8.7 Culture for 3-hydroxypropionate Production

Performances of strains were assessed in 500 ml baffled Erlenmeyer flask cultures using modified M9 medium (Anderson, 1946, Proc. Natl. Acad. Sci. USA 32:120-128) that was supplemented with 4,5 mM threonine, 5 mM methionine, 10 g/l MOPS and 10 g/l glucose and adjusted to pH 6,8. Spectinomycin and/or kanamycin were added if necessary at a concentration of 50 mg/l, and/or chloramphenicol was added if necessary at a concentration of 60 mg/l. 100 μM IPTG was also added for induction of the expression vector pME101, if present. A 24 hours preculture was used to inoculate a 50 ml culture to an $OD_{600nm}$ of about 0,1. The cultures were kept on a shaker at 37° C. and 200 rpm until the glucose in the culture medium was exhausted. At the end of the culture, glucose and major products were analyzed by HPLC using a Biorad HPX 97H column for the separation and a refractometer for the detection. Production of 3-hydroxypropionate was confirmed by LC/MS/MS.

The performances of the different strains are given in table below.

| Culture ref | Strain_ref | Genotype | Growth rate ($h^{-1}$) | [3-hydroxypropionate] (mM) |
|---|---|---|---|---|
| FbDI421 | DI0084c02 | MG1655 DpykF DmetA DthrLABC | 0.264 | 0.09 |
| FbDI389 | DI0126c01 | MG1655 DpykF DmetA DthrLABC (pME101-thrA*1-serC) (pBBR1MCS5-Ptrc01/RBS01*2-ald4-kivDII-TT07) | 0.159 | 1.46 |
| FbDI391 | DI0127c01 | MG1655 DpykF DmetA DthrLABC (pME101-thrA*1-serC) (pBBR1MCS5-Ptrc01/RBS01*2-aldH-kivDII-TT07) | 0.181 | 1.09 |
| FbDI393 | DI0123c01 | MG1655 DpykF DmetA DthrLABC (pBBR1MCS5-Ptrc01/RBS01*2-gabD-kivDII-TT07) (pME101-thrA*1-serC) | 0.182 | 0.76 |

EXAMPLE 9

Construction of strains with increased 4-hydroxybutyrate pathway flux expressing a 2-keto acid decarboxylase, a hydroxy aldehyde reductase, an aldehyde/alcohol dehydrogenase and a 4-oxoglutaryl-CoA-synthetase encoding genes: MG1655 ΔsucAB ΔaceBAK ΔarcA ΔgdhA (pBBR1MCS5-Ptrc01/RBS01*2-aldH-kivDll-TT07) (pUC19-Ptrc01/OP01/RBS01-adhE2ca-prpE)

9.1 Construction of the strain MG1655 ΔaceBAK ΔsucAB

To delete the aceBAK genes, the homologous recombination strategy described by Datsenko & Wanner (2000) was used as previously described. For this purpose the following oligonucleotides were used:

ΔaceBAKF (SEQ ID NO 35):
ctggctttcacaaggccgtatggcgagcaggagaagcaaattcttactgccgaagcggtagaatttctgactgagctggtTGTA
GGCTGGAGCTGCTTCG with
- a region (lower case) homologous to the sequence (4213531-4213610) of the MG1655 aceB region (reference sequence on the website www.ecogene.org/),
- a region (upper bold case) for the amplification of the kanamycin resistance cassette, ΔaceBAKR (SEQ ID NO 36):
aacatcttccacatgcccttcacgtatgcggttttgtagtgcgcgcc agtaatcagcgcggaacaggtcggcgtgcatcCATATGAATATCCTC

CTTAG with
- a region (lower case) homologous to the sequence (4218298-4218220) of the MG1655 aceK region (reference sequence on the website www.ecogene.org/),
- a region (upper bold case) for the amplification of the kanamycin resistance cassette.

The oligonucleotides ΔaceBAKF and ΔaceBAKR were used to amplify the kanamycin resistance cassette from the plasmid pKD4. The PCR product obtained was then introduced by electroporation into the strain MG1655 (pKD46). The kanamycin resistant transformants were then selected and the insertion of the resistance cassette was verified by a PCR analysis with the oligonucleotides aceBAKF and aceBAKR defined below. The strain retained was designated MG1655 ΔaceBAK::Km.

aceBAKF (SEQ ID NO 37):
cgttaagcgattcagcaccttacc
(homologous to the sequence from 4213251 to 4213274).

aceBAKR (SEQ ID NO 38):
aacgcattacccactctgttaatacg
(homologous to the sequence from 4218728 to 4218702).

To delete the sucAB genes, the homologous recombination strategy described by Datsenko & Wanner (2000) was used as previously described. For this purpose the following oligonucleotides are used:

ΔsucABF (SEQ ID NO 39):
GCGCTTTGAAAGCCTGGTTGGACTCTTCTTACCTCTCTGGCGCAAACCA

GAGCTGGATAGAACAGCTCTATGAAGACTTCTGTAGGCTGGAGCTGCTT

CG with
- a region (upper case) homologous to the sequence (757939-758018) of the MG1655 sucAB region (reference sequence on the website www.ecogene.org/),
- a region (upper bold case) for the amplification of the chloramphenicol resistance cassette ΔsucABR (SEQ ID NO 40):
CCAGCAGCAGACGCGTCGGATCTTCCAGCAACTCTTTGATCGTTACCAG

GAAGCCCACGGATTCGCGACCATCGATCAGCATATGAATATCCTCCTTA

G with
- a region (upper case) homologous to the sequence (761954-761876) of the MG1655 sucAB region (reference sequence on the website www.ecogene.org/),
- a region (upper bold case) for the amplification of the chloramphenicol resistance cassette.

The oligonucleotides DsucABF and DsucABR were used to amplify the chloramphenicol resistance cassette from the plasmid pKD3. The PCR product obtained was then introduced by electroporation into the strain MG1655 (pKD46). The chloramphenicol resistant transformants were then selected and the insertion of the resistance cassette was verified by a PCR analysis with the oligonucleotides sucABF and sucABR defined below. The strain retained was designated MG1655 ΔsucAB::Cm.

sucABF (SEQ ID NO 41): GGCGTAACAAAGAAATGCAGG
    (homologous to the sequence from 757747 to
    757767).

sucABR (SEQ ID NO 42): GCTTCAACCAGAATCTGG
    (homologous to the sequence from 762535 to
    762518).

To transfer the ΔaceBAK::Km, the method of phage P1 transduction was used. The preparation of the phage lysate from the strain MG1655 ΔaceBAK::Km was used for the transduction into the strain MG1655 ΔsucAB::Cm.

The kanamycin and chloramphenicol resistant transformants were then selected and the ΔaceBAK::Km was verified by a PCR analysis with the previously defined oligonucleotides aceBAKF/aceBAKR and sucABF/sucABR. The strain retained was designated MG1655 ΔsucAB::Cm ΔaceBAK::Km.

The kanamycin and chloramphenicol resistance cassettes were eliminated. The plasmid pCP20 carrying FLP recombinase acting at the FRT sites of the kanamycin and chloramphenicol resistance cassettes was then introduced into the recombinant strain by electroporation. After a series of cultures at 42° C., the loss of the kanamycin and chloramphenicol resistance cassettes was verified by a PCR analysis with the same oligonucleotides as used previously (aceBAKF/aceBAKR, and sucABF/sucABR). The strain retained was designated MG1655 ΔsucAB ΔaceBAK.

9.2 Construction of the strain MG1655 ΔsucAB ΔaceBAK ΔarcA ΔgdhA

To delete the arcA gene, the homologous recombination strategy described by Datsenko & Wanner (2000) was used. For this purpose the following oligonucleotides were used:

ΔarcAF (SEQ ID NO 43):
cccgcacattcttatcgttgaagacgagttggtaacacgcaacacgttg aaaagtattttcgaagcggaaggctatgTGTAGGCTGGAGCTGCTTCG with
- a region (lower case) homologous to the sequence (4638322-4638245) of the MG1655 arcA region (reference sequence on the website www.ecogene.org/),
- a region (upper case) for the amplification of the kanamycin resistance cassette ΔarcAR (SEQ ID NO 44):
ccagatcaccgcagaagcgataaccttcaccgtgaatggtggcgatgatt tccggcgtatccggcgtagattcgaaatgCATATGAATATCCTCCTTAG with
- a region (lower case) homologous to the sequence (4637621-4637699) of the MG1655 arcA region (reference sequence on the website www.ecogene.org/),
- a region (upper case) for the amplification of the kanamycin resistance cassette The oligonucleotides DarcAF and DarcAR were used to amplify the kanamycin resistance cassette from the plasmid pKD4. The PCR product obtained was then introduced by electroporation into the strain MG1655 (pKD46). The kanamycin resistant transformants were then selected and the insertion of the resistance cassette was verified by a PCR analysis with the oligonucleotides arcAF and arcAR defined below. The strain retained was designated MG1655 ΔarcA::Km.

arcAF (SEQ ID NO 45): cgacaattggattcaccacg
    (homologous to the sequence from 4638746 to
    4638727).

arcAR (SEQ ID NO 46): gcggtattgaaaggttggtgc
    (homologous to the sequence from 4637308 to
    4637328).

To transfer the ΔarcA::Km, the method of phage P1 transduction was used. The preparation of the phage lysate from the strain MG1655 ΔarcA::Km was used for the transduction into the strain MG1655 ΔsucAB ΔaceBAK.

The kanamycin resistant transformants were then selected and the ΔarcA::Km was verified by a PCR analysis with the previously defined oligonucleotides arcAF and arcAR. The strain retained was designated MG1655 ΔsucAB ΔaceBAK ΔarcA::Km.

To delete the gdhA gene, the homologous recombination strategy described by Datsenko & Wanner (2000) was used. The oligonucleotides ΔgdhAF and ΔgdhAR were used to amplify the chloramphenicol resistance cassette from the plasmid pKD3.

ΔgdhAF (SEQ ID NO 47):
taaacaacataagcacaatcgtattaatatataagggttttatatctat gTGTAGGCTGGAGCTGCTTCG with
- a region (lower case) homologous to the sequence (1840348 to 1840397) of the MG1655 gdhA region (reference sequence on the website www.ecogene.org/),
- a region (upper bold case) for the amplification of the chloramphenicol resistance cassette ΔgdhAR (SEQ ID NO 48):
taagcgtagcgccatcaggcatttacaacttaaatcacaccctgcgcca
gCATATGAATATCCTCCTTAG with:
- a region (lower case) homologous to the sequence (1841767 to 1841718) of the MG1655 gdhA region (reference sequence on the website www.ecogene.org/),
- a region (upper bold case) for the amplification of the chloramphenicol resistance cassette.

The PCR product obtained was then introduced by electroporation into the MG1655 (pKD46) strain. The chloramphenicol resistant transformants were then selected and the insertion of the resistance cassette was verified by a PCR analysis with oligonucleotides Ptrc-gdhAverF and gdhA R. The strain obtained was named MG1655 ΔgdhA::Cm Ptrc-gdhAverF (SEQ ID NO 49):
CCTTAACGTTATTGTCTCTGC: homologous to the sequence (from 1840168 to 1840188)

gdhA R (SEQ ID NO 50):
GGAGGAAGCCCCAGAGCAGG: homologous to the sequence (from 1842274 to 1842293).

To transfer the ΔgdhA::Cm, the method of phage P1 transduction was used. The preparation of the phage lysate from the strain MG1655 ΔgdhA::Cm was used for the transduction into the strain MG1655 ΔsucAB ΔaceBAK ΔarcA::Km.

The kanamycin and chloramphenicol resistant transformants were then selected and the ΔgdhA::Cm was verified by a PCR analysis with the previously defined oligonucleotides Ptrc-gdhAverF and gdhA R. The strain retained was designated MG1655 ΔsucAB ΔaceBAK ΔarcA::Km ΔgdhA::Cm.

The kanamycin and chloramphenicol resistance cassettes were eliminated. The plasmid pCP20 carrying FLP recombinase acting at the FRT sites of the kanamycin and chloramphenicol resistance cassettes was then introduced into the recombinant strain by electroporation. After a series of cultures at 42° C., the loss of the kanamycin and chloramphenicol resistance cassettes was verified by a PCR analysis with the same oligonucleotides as used previously (aceBAKF/aceBAKR, sucABF/sucABR, arcAF/arcAR and gdhAverF/gdhA R). The strain retained was designated MG1655 ΔsucAB ΔaceBAK ΔarcA ΔgdhA.

9.3 Construction of a Plasmid for Overexpression of the Bifunctional Aldehyde/Alcohol Dehydrogenase adhE2 of *Clostridium acetobutylicum* and the 4-oxoglutaryl-CoA-synthetase: pUC19-Ptrc01/OP01/RBS01-adhE2ca-prpE-TT02

The adhE2 gene from *Clostridium acetobutylicum* coding for the bifunctional aldehyde/alcohol dehydrogenase is cloned in the plasmid pUC19. The prpE gene from *Escherichia coli* coding for the propionyl-CoA synthetase is cloned downstream adhE2ca. The adhE2 gene is PCR amplified from the megaplasmid pSoll of the *Clostridium acetobutylicum* strain ATCC824 (33722 to 36298: reference sequence gb_AF321779.1) with the oligonucleotides adhE2Ca F and adhE2Ca R.

adhE2Ca F (SEQ ID NO 51):
ggtaccggatccgggcccgagctgttgacaattaatcatccggctcgta taatgtgtgg*aattgtgagcggataacaattTACGTA*taaggaggtata ttATGAAAGTTACAAATCAAAAAGAAC with
- a region (bold lower case) harbouring a KpnI, BamHI, ApaI restriction sites
- a region (underlined lower case) harbouring the promoter Ptrc
- a region (italic lower case) harbouring an operator sequence
- a region (italic upper case) harbouring a SnaBI restriction site
- a region (lower case) harbouring a Ribosome Binding Site sequence
- a region (underlined bold upper case) homologous the *C. acetobutylicum* adhE2 region from 33722 to 33752 (reference sequence gb_AF321779.1)

adhE2Ca R (SEQ ID NO 52):
GAGCTCAAGCTTaacagataaaacgaaaggcccagtctttcgactgagc

*ctttcgttttatttgatg*cctagggctagctctagattaa*TTAAAATGA*

TTTTATATAGATATCCTTAAGTTCAC, with
- a region (upper case) harbouring a HindIII, SacI restriction sites.
- a region (underlined bold lower case) harbouring a transcriptional terminator (*E. coli* rrnB T₁ gene transcription terminator: Orosz A, Boros I and Venetianer P. Eur. J. Biochem. 1991 Nov. 1; 201(3):653-9)
- a region (italic case) harbouring the PacI, XbaI, NheI, AvrII restriction sites
- a region (underlined upper case) homologous the *C. acetobutylicum* adhE2 region from 36264 to 36298 (reference sequence gb_AF321779.1)

This PCR fragment is digested with BamHI and HindIII and cloned into the vector pUC19 digested with the same enzymes. The plasmid obtained is named pUC19-Ptre01/OP01/RBS01-adhE2ca-TT02

To amplify prpE gene, PCR is carried out using genomic DNA of *E. coli* MG1655 as template and the primers prpE F and prpE R.

prep F (SEQ ID NO 53):
<u>tctagaggatcc</u>aagttcaacaggagagcattatg with
- a region (bold underlined case) harbouring a XbaI and BamHI restriction sites
- a region (lower case) homologous to the sequence (351910 to 351932) of the MG1655 prpE region (reference sequence on the website www.ecogene.org/), prep R_(SEQ ID NO 54):
<u>ggatccgctaccctaggtacgta</u>ctactcttccatcgcctggc

- a region (bold underlined case) harbouring a BamHI, NheI, AvrII, SnaBII restriction sites
- a region (lower case) homologous to the sequence (353816 to 353797) of the MG1655 prpE region (reference sequence on the website www.ecogene.org/), This PCR fragment is digested with XbaI and NheI and cloned into the vector pUC19-Ptrc01/OP01/RBS01-adhE2ca-TT02 digested with the same enzymes. The plasmid obtained is named pUC19-Ptrc01/OP01/RBS01-adhE2ca-prpE-TT02.

9.4 Construction of the strain MG1655 ΔsucAB ΔaceBAK ΔarcA ΔgdhA (pBBR1MCS5Ptrc01/RBS01*2-aldH-kivD1'-TT07) (pUC19-Ptrc01/OP01/RBS01-adhE2ca-prpE-TT02)

The pBBR1MCS5-Ptrc01/RBS01*2-aldH-kivDll-TT07 and the pUC19-Ptrc01/OP01/RBS01-adhE2ca-prpE-TT02 plasmids are then introduced into the strain MG1655 ΔsucAB ΔaceBAK ΔarcA ΔgdhA.

9.5 Culture for 4-hydroxybutyrate Production

Performances of strains are assessed in 500 ml baffled Erlenmeyer flask cultures using modified M9 medium (Anderson, 1946, Proc. Natl. Acad. Sci. USA 32:120-128) that is supplemented with 5 g/l succinic acid, 40 g/l MOPS and 10 g/l glucose and adjusted at pH 6,8. Spectinomycin and/or kanamycin are added if necessary at a concentration of 50 mg/l, and/or chloramphenicol is added if necessary at a concentration of 60 mg/l. 100 μM IPTG is also added for induction of the expression vector pME101, if present. A 24 hours preculture is used to inoculate a 50 ml culture to an $OD_{600nm}$ of about 0.1 to 0,3. The cultures are kept on a shaker at 37° C. and 200 rpm until the glucose in the culture medium is exhausted. At the end of the culture, glucose and major products are analyzed by HPLC using a Biorad HPX 97H column for the separation and a refractometer for the detection. Production of 4-hydroxy-butyrate is confirmed by LC/MS/MS.

References

Datsenko, K. A. & Wanner, B. L. (2000) "One-step inactivation of chromosomal genes in *Escherichia coli* K-12 using PCR products". *Proc. Natl. Acad. Sci. USA* 97: 6640-6645

Anderson, 1946, *Proc. Natl. Acad. Sci. USA* 32:120-128

Miller, 1992; "A Short Course in Bacterial Genetics: A Laboratory Manual and Handbook for *Escherichia coli* and Related Bacteria", *Cold Spring Harbor Laboratory Press, Cold Spring Harbor, N.Y.*

Schaefer et al. 1999, *Anal. Biochem.* 270: 88-96

Liebl et al., 1989, *Appl. Microbiol. Biotechnol.* 32: 205-210

Riedel et al. 2001, *J. Mol. Microbiol. Biotechnol.* 3: 573-583

C E Ballou; H Hesse; R Hesse; (1956). "The Synthesis and Properties of Hydroxypyruvic Acid Phosphate" *J Am Chem. Soc.,* 78 (15), 3718-3720.

M. E. Kovach, (1995), *Gene* 166:175-176

Harrington K. J., Laughlin R. B. and Liang S. *Proc Natl Acad Sci USA.* 2001 Apr. 24; 98(9):5019-24.

The invention claimed is:

1. A microorganism genetically modified for the bioproduction of a hydroxy acid of formula (I) wherein the microorganism comprises a two-step metabolic pathway for said hydroxy acid from a hydroxy-2-keto-aliphatic acid of formula (II) through an intermediate hydroxy-aldehyde of formula (III):

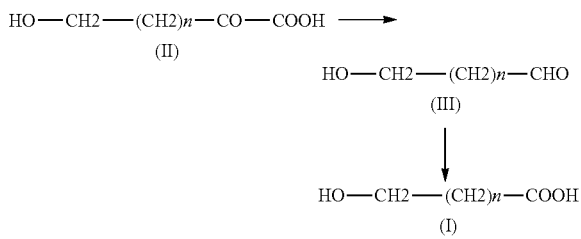

with n = 0, 1, or 2,
wherein
EA1 is an enzyme having a 2-keto-acid decarboxylase activity, and
EA2 is an enzyme having hydroxy aldehyde dehydrogenase activity, wherein said enzyme EA1 is encoded by a heterologous gene, and wherein producing said hydroxy-2-keto-aliphatic acid of formula (II) is increased in said microorganism by increasing the level of expression of at least one of the following enzymes: serine transaminase, serine oxidase, 3-phosphohydroxypyruvate phosphatase, homoserine transaminase, homoserine oxidase, 4-oxoglutaryl-CoA synthetase, and alcohol dehydrogenase.

2. The microorganism of claim 1, wherein the endogenous genes encoding for hydroxy aldehyde reductase activity have been deleted in said microorganism.

3. The microorganism of claim 1, wherein said hydroxy acid of formula (I) is 3-hydroxypropionate and said hydroxy-2-keto-aliphatic acid of formula (II) is 4-hydroxy-2-ketobutyrate.

4. The microorganism of claim 1, wherein said hydroxy acid of formula (I) is hydroxyacetate and said hydroxy-2-keto-aliphatic acid of formula (II) is hydroxypyruvate.

5. The microorganism of claim 1, wherein said hydroxy acid of formula (I) is 4-hydroxybutyrate and said hydroxy-2-keto-aliphatic acid of formula (II) is 5-hydroxy-2-ketopentanoate.

6. The microorganism according to claim 1, wherein said microorganism is selected from the group consisting of bacterium, yeast and fungus.

7. The microorganism of claim 6, wherein said microorganism is a bacterium that is selected from the group consisting of Enterobacteriaceae, Clostridiaceae, Bacillaceae, Streptomycetaceae and Corynebacteriaceae.

8. The microorganism of claim 4, wherein producing hydroxypyruvate of formula (II) is increased in said microorganism by increasing the level of expression of at least one of the following enzymes: serine transaminase, serine oxidase, and 3-phosphohydroxypyruvate phosphatase.

9. The microorganism of claim 5, wherein producing 5-hydroxy-2-ketopentanoate of formula (II) is increased in said microorganism by increasing the level of expression of at least one of the following enzymes: 4-oxoglutaryl-CoA synthetase and alcohol dehydrogenase.

10. The microorganism of claim 9, wherein 4-oxyglutaryl-CoA synthetase is increased.

11. The microorganism of claim 3, wherein producing 4-hydroxy-2-ketobutyrate of formula (II) is increased in said microorganism by increasing the level of expression of at least one of the following enzymes: homoserine transaminase and homoserine oxidase.

12. A method for the fermentative production of an hydroxy acid of formula (I), comprising:
culturing a microorganism according to claim 1, on an appropriate culture medium comprising a source of carbon; and
recovering the hydroxy acid from the culture medium.

13. The method of claim 12, wherein said hydroxy acid is further purified.

14. The method of claim 12, wherein the source of carbon is selected from the group consisting of monosaccharides, disaccharides, oligosaccharides, molasses, starch, hemicelluloses, glycerol and combinations

* * * * *